(12) United States Patent
Anderson et al.

(10) Patent No.: US 9,487,751 B2
(45) Date of Patent: Nov. 8, 2016

(54) METHOD TO ISOLATE, IDENTIFY, AND USE EMBRYONIC STEM CELLS DIRECTED TO FOREBRAIN INTERNEURON FATE

(75) Inventors: Stewart A. Anderson, New York, NY (US); Asif Maroof, New York, NY (US); Lorenz Studer, New York, NY (US)

(73) Assignees: CORNELL UNIVERSITY, Ithaca, NY (US); SLOAN KETTERING INSTITUTE FOR CANCER RESEARCH, New York, NY (US)

(*) Notice: Subject to any disclaimer, the term of this patent is extended or adjusted under 35 U.S.C. 154(b) by 9 days.

(21) Appl. No.: 13/376,039

(22) PCT Filed: Jun. 2, 2010

(86) PCT No.: PCT/US2010/037118
§ 371 (c)(1),
(2), (4) Date: Feb. 16, 2012

(87) PCT Pub. No.: WO2010/141622
PCT Pub. Date: Dec. 9, 2010

(65) Prior Publication Data
US 2012/0148549 A1    Jun. 14, 2012

Related U.S. Application Data

(60) Provisional application No. 61/183,417, filed on Jun. 2, 2009.

(51) Int. Cl.
| | |
|---|---|
| C12N 5/10 | (2006.01) |
| C12N 15/113 | (2010.01) |
| C12N 15/63 | (2006.01) |
| C12N 5/079 | (2010.01) |
| C12N 5/0793 | (2010.01) |
| A61K 35/30 | (2015.01) |
| A61K 35/12 | (2015.01) |

(52) U.S. Cl.
CPC ............ *C12N 5/0619* (2013.01); *A61K 35/30* (2013.01); *A61K 35/12* (2013.01); *C12N 2500/44* (2013.01); *C12N 2501/115* (2013.01); *C12N 2501/15* (2013.01); *C12N 2501/155* (2013.01); *C12N 2501/41* (2013.01); *C12N 2506/02* (2013.01); *C12N 2506/45* (2013.01); *C12N 2510/00* (2013.01); *C12N 2533/90* (2013.01)

(58) Field of Classification Search
None
See application file for complete search history.

(56) References Cited

U.S. PATENT DOCUMENTS

| | | |
|---|---|---|
| 2004/0265849 A1 | 12/2004 | Cargill et al. |
| 2007/0254359 A1 | 11/2007 | Rezania et al. |
| 2007/0281355 A1 | 12/2007 | Dalton et al. |

OTHER PUBLICATIONS

Cobos et al, Cellular Patterns of Transcription Factor Expression in Developing Cortical Interneurons, Cerebral Cortex 2006;16:i82--i88.*
Du et al, NKX2.1 specifies cortical interneuron fate by activating Lhx6, Development 135, 1559-1567 (2008).*
Li et al, Regional Distribution of Cortical Interneurons and Development of Inhibitory Tone Are Regulated by Cxcl12/Cxcr4 Signaling, J Neurosci. Jan. 30, 2008; 28(5): 1085-1098.*
Li et al, supplemental data and figure 1, J Neurosci. Jan. 30, 2008; 28(5): supplemental pp. 1-3.*
Arber and Li, Cortical interneurons from human pluripotent stem cells: prospects for neurological and psychiatric disease,12086397 Front. Cell. Neurosci. 7:10, pp. 1-11.*
Batista-Brito et al. "Gene Expression in Cortical Interneuron Precursors is Prescient of their Mature Function," Cerebral Cortex 18:2306-2317 (2008).
PCT International Search Report for PCT/US10/37118, filed Jun. 2, 2010.
PCT International Written Opinion ofr PCT/US10/37118, filed Jun. 2, 2010.
Watanabe et al., "Directed Differentiation of Telencephalic Precursors from Embryonic Stem Cells," Nat. Neurosci. 8 (3):288-296 (2005).
Wonders et al., "The Origin and Specification of Cortical Interneurons," Nat. Rev. 7:687-696 (2006).
Maroof et al., "Prospective Isolation of Cortical Interneuron Precursors from Mouse Embryonic Stem Cells," J. Neurosci. 30(13):4667-4675 (2010).
Wonders et al., "A Spatial Bias for the Origins of Interneuron Subgroups within the Medial Ganglionic Eminence," Dev. Biol. 314(1):127-136 (2008).
Tomishima et al., "Production of Green Fluorescent Protein Transgenic Embryonic Stem Cells Using the Gensat Bacterial Artificial Chromosome Library," Stem Cells 25:39-45 (2007).
Wataya et al., "Minimization of Exogenous Signals in ES Cell Culture Induces Rostral Hypothalamic Differentiation," Proc. Nat. Am. Sci. 105(33):11796-11801 (2008).
Fogarty et al., "Spatial Genetic Patterning of the Embryonic Neuroepithelium Generates GABAergic Interneuron Diversity in the Adult Cortex," J. Neurosci. 27(41):10935-10946 (2007).
Alvarez-Dolado et al., "Cortical Inhibition Modified by Embryonic Neural Precursors Grafted into the Postnatal Brain," J. Neurosci. 26(28):7380-7389 (2006).
Wichterle et al., "Young Neurons from Medial Ganglionic Eminence Disperse in Adult and Embryonic Brain," Nat. Neurosci. 2(5):461-466 (1999).

(Continued)

*Primary Examiner* — Maria Marvich
(74) *Attorney, Agent, or Firm* — LeClairRyan, a Professional Corporation

(57) ABSTRACT

The present invention relates to methods of isolating a purified or enriched population of cortical or striatal immature interneuron progenitor cells and the isolated purified or enriched population of immature interneuron progenitor cells. Methods of treating a condition mediated by a loss or deficiency of interneuron function using the purified or enriched population of immature interneuron progenitor cells are also disclosed.

4 Claims, 14 Drawing Sheets

(56) References Cited

OTHER PUBLICATIONS

Cobos et al., "Mice Lacking Dlx1 Show Subtype-Specific Loss of Interneurons, Reduced Inhibition and Epilepsy," Nat. Neurosci. 8(8):1059-1068 (2005).

Xu et al., "Cortical Interneuron Fate Determination: Diverse Sources for Distinct Subtypes?" Cerebral Cortex 13:670-676 (2003).

Wichterle et al., "Permissive Corridor and Diffusible Gradients Direct Medial Ganglionic Eminence Cell Migration to the Neocortex," Proc. Nat. Am. Sci. 100(2):727-732 (2003).

* cited by examiner

METHOD TO ISOLATE, IDENTIFY, AND USE EMBRYONIC STEM CELLS DIRECTED TO FOREBRAIN INTERNEURON FATE

This application is a national stage application under 35 U.S.C. §371 of PCT Application No. PCT/US2010/37118, filed Jun. 2, 2010, which claims the benefit of U.S. Provisional Patent Application Ser. No. 61/183,417, filed Jun. 2, 2009, which is hereby incorporated by reference in its entirety.

This invention was made with government support under grant number IF 31 MH0 79664-01A1 awarded by the National Institute of Mental Health and grant number 5R01MH066912 awarded by the National Institutes of Health. The government has certain rights in this invention.

FIELD OF THE INVENTION

The present invention relates to methods of isolating and using a purified or enriched population of cortical or striatal immature interneuron progenitor cells.

BACKGROUND OF THE INVENTION

The cerebral cortex is involved in higher-order cognitive processing, learning, and memory. These functions are mediated by excitatory projection neurons and inhibitory interneurons. Interneurons, which comprise approximately 20% of the cortical neurons (Krimer et al., "Prefrontal Microcircuits: Membrane Properties and Excitatory Input of Local, Medium, and Wide Arbor Interneurons," J Neurosci 21(11):3788 (2001)), can be divided into subgroups based on neurochemical markers, connectivity, and physiological properties.

GABA(γ-aminobutyric acid)ergic interneurons play crucial roles in nearly all aspects of brain function. By providing the major source of inhibitory circuitry in the cerebral cortex, GABAergic interneurons are required for the synchronous activity necessary to generate sustained oscillations among neurons within a network that are essential during perception, coordinated movement, learning and memory. Cortical deficits in inhibitory neuronal transmission have been implicated in several neurological and psychiatric disorders including epilepsy, autism, and schizophrenia.

Previous studies have demonstrated that cortical interneuron precursors have an amazing ability to migrate, mature, and function after transplantation into adult cerebral cortex. Since these cells normally control cortical activity, it has been proposed to use them in a cell based therapy for chronic seizures of focal origin. Particularly in the case of intractable seizure disorders, cell-based therapy has been proposed as an alternative to surgical intervention. It is anticipated that such cells can also be used in cell-based therapy for forebrain disorders such as medication-intractable seizures and Parkinson's disease. Such therapy could be used either to harness the intrinsic ability of these cells to inhibit activity, or a drug delivery system after genetic manipulation to express therapeutic agents (i.e., agents that suppress seizures, including GABA, neuropeptide Y, adenosine). However, the practical use of interneuron precursors in preclinical or clinical studies requires the ability to generate very large numbers of these cells, which currently does not exist.

The present invention is directed to overcoming these and other deficiencies in the art.

SUMMARY OF THE INVENTION

A first aspect of the present invention relates to a method of isolating an enriched or purified population of mammalian cortical or striatal immature interneuron precursor cells from an isolated population of cells. This method involves providing an isolated population of cells and selecting a promoter and/or enhancer region which specifically functions in cortical or striatal immature interneuron precursor cells, but not the isolated population of cells. The method further involves introducing a nucleic acid molecule encoding a marker protein under control of the promoter and/or enhancer region into the isolated population of cells and inducing production of cortical or striatal immature interneuron precursor cells from the isolated population of cells. The cortical or striatal immature interneuron precursor cells are allowed to express the marker protein, and the cells expressing the marker protein are separated from the induced isolated population of cells, thereby isolating an enriched or purified population of cortical or striatal immature interneuron precursor cells.

Another aspect of the invention relates to an enriched or purified preparation of mammalian cortical or striatal immature interneuron precursor cells expressing Lhx6. Related aspects of the invention include methods of treating a condition mediated by a deficiency or loss of cortical or striatal interneuron function and targeting the delivery of a therapeutic agent using the enriched or purified population of mammalian cortical or striatal immature interneurons.

BRIEF DESCRIPTION OF THE DRAWINGS

FIG. 1B is a model of the transcriptional profile of interneuronal precursors migrating in the developing telencephalon, as viewed through a coronal section at E13.5. FoxG1 (aka BF1) is expressed throughout the telencephalon, while Nkx2.1 is expressed in the medial ganglionic eminence (MGE) and the pre-optic area. Nkx6.2 is detectable in the dorsal-most region of the MGE. Lhx6 is continuously expressed from the post-mitotic state through adulthood. FIGS. 1C-1E are fluorescent photomicrographs of mESCs differentiated with the ventral telencephalon protocol for 12 days and immunolabeled with the indicated transcriptional marker. FIG. 1C shows expression of the telencephalic marker FOXG1. Many of the FOXG1-expressing cells also express the MGE marker NKX2.1 (yellow) as shown in the FIG. 1C1. This co-labeling supports the notion that the ventral telencephalon protocol is predominantly generating NKX2.1+ progenitors of the telencephalon rather than those of the ventral diencephalon (hypothalamus) that would be FOXG1 negative. As shown in FIG. 1D, LHX6+ cells appear to be streaming from an NKX2.1+ cluster. FIGS. 1E and 1F show differentiated cells from the Lhx6::GFP reporter mES line. The GFP+ cells appear to be streaming out of a Nkx2.1+ progenitor domain (FIG. 1E), and these cells co-label for LHX6 protein (see FIG. 1F showing LHX6 expression alone and FIG. 1F1 showing co-labeling of LHX6 and GFP in the same field). FACS analysis (FIG. 1G) of the Lhx6::GFP line differentiated until day 12 shows a GFP+ population clearly segregating from the autofluorescent background. Yield based on FACS (GFP+ cells whose viability is established by DAPI exclusion) is ~2%. In FIG. 1H, GFP+ cells were collected by FACS, plated on glass coverslips, fixed and immunolabeled for the indicated markers. The Lhx6::GFP+ cells generally express the telencephalic marker FOXG1, the inhibitory neurotransmitter GABA, LHX6, and the ventral telencephalic marker DLX2. There was minimal (less than 1%) co-labeling for the dorsal telencephalic markers PAX6 or TBR1. Scale bar in FIGS. 1C, 1D, 1E=20 um; Scale bar 1F=10 um.

FIG. 3A shows immunofluorescence labeling for GFP in a 50 μm coronal section depicting the location of an injection site 1 day following transplantation into neonatal cortex. FIGS. 6B-6E, all show the same view of the cell indicated by the arrow in FIG. 6A immunolabeled for Ki67 (FIG. 6B), GFP (FIG. 6C), and DAPI (FIG. 6D). FIG. 6E is a merged image showing the co-labeling of Ki67, GFP, and DAPI. Co-labeling of GFP and the cell cycle marker Ki67 is very rare (less than 2%), indicating that Lhx6::GFP+ cells have generally exited the cell cycle either before or shortly after the time of transplantation. No evidence of tumor formation was found in any of the over two dozen transplantations that have been evaluated 1-240 days following transplantation.

FIGS. 4A-4C are photomicrographs showing immunofluorescence labeling of GFP in 50 μm coronal sections at various days post transplant (DPT). Arrows indicate cells shown at higher magnification in the insets (FIGS. 4D-4F). At 1 DPT, the GFP+ cells were distributed close to the injection site, and many appear to be migrating into the cortical parenchyma (FIG. 4A). At 7 DPT, the GFP+ cells are much more broadly distributed, and many have multipolar morphologies suggestive of post-migratory neurons (FIG. 4B). At 30 DPT, the GFP+ cells mainly exhibit interneuronal morphologies (FIGS. 4C and 4F). The medio-lateral extent of these cells at 30 DPT is 2.5 mm+/−0.3 mm. FIGS. 4G-4I are graphs showing the distributions of transplanted cells at 1 DPT (FIG. 4G, n=3), 7 DPT (FIG. 4H, n=4), or 30 DPT (FIG. 4I, n=5). The x-axes show rostral-caudal distance from the injection site. The y-axes show cell profile number per 250 μm bin made conservatively by multiplying the number of GFP+ cell profiles in the most distal section of that bin by 5. In FIG. 4I, the Y-axis extends to only 100 cells. After 1 DPT, the bulk of transplanted cells are within 300 um of the injection site (FIG. 4G). By 7 DPT, some of the cells have dispersed as far as 2 mm from the injection site (FIG. 4H). Although the survival or detectability of GFP+ cells had significantly decreased by 30 DPT, the R-C distribution is roughly equivalent to that seen at 7 DPT (FIG. 4I). Scale bar=200 μm in FIGS. 4A, 400 μm in 4B and 4C.

FIG. 5A is a low magnification view of GFP+ cells with interneuron-like morphologies. The GFP+ cells mainly exhibit multipolar, aspiny morphologies commonly present in cortical interneurons. Scale bar, 100 μm. FIGS. 5B and 5B1 are the same field showing that the majority of transplanted cells (>85%) express GABA (FIG. 5B) (GABA and GFP co-labeling shown in FIG. 5B1). FIGS. 5C-5C3 are confocal images of a section labeled for GFP (FIG. 5C), neuropeptide Y (NPY) (FIG. 5C1), and somatostatin (SST) (FIG. 5C2; merged image in FIG. 5C3). As occurs ex vivo, there is partial overlap between the NPY+ and SST+ interneuron subgroups (arrowheads show SST-expressing ES-derived cells, small arrows indicate cells that coexpress NPY). FIGS. 5D and 5D1 show the colabeling of two GFP+ cells with parvalbumin (PV) (arrows in FIG. 5D show colabeled cells in FIG. 5D1). As expected, the Lhx6::GFP and PV+ colabeled cells do not express SST (blue pseudocolor from Cy5 signal), but express the potassium channel KV3.1 as shown in FIGS. 5E (PV labeling alone), 5E1 (Kv3.1 labeling alone) and 5E2 (GFP, PV, and Kv3.1 co-labeling).

FIGS. 6A-6K demonstrate that mES-derived, Lhx6-GFP+ cells exhibit physiological and neurochemical characteristics of cortical interneurons. Lhx6-GFP cells were differentiated and transplanted as in FIG. 5. Twenty-two days after transplantation, slices from these animals were subjected to whole-cell patch-clamp recordings and fluorescence labeling. FIG. 6A shows the spontaneous synaptic inputs recorded from a GFP+ cell voltage-clamped at −60 mV. FIGS. 6B-6K depict the neurochemical profiles and physiological responses of two transplanted cells. Images are formed from collapsed stacks taken by confocal microscopy. FIGS. 6B and 6G are monochrome images of the Neurobiotin-streptavidin-Alexa 546 signals. Higher-magnification views are shown in FIGS. 6C-6C3 and 6H-6H3, where the Neurobiotin (NB) signal (FIGS. 6C2, 6H2) has been pseudo-colored blue to demonstrate that the same cell soma is being imaged as that shown at lower magnification. These cells were subjected to electrophysiological recordings, with current injection protocols testing threshold current injection (FIGS. 6D and 6I), response to hyperpolarizing current injection and 2x threshold (FIGS. 6E and 6J), and suprathreshold (5x) current injection that elicited discharge of action potentials at a near-maximal firing frequency (FIGS. 6F and 6K). The cell in FIG. 6B colabels for GFP (FIG. 6C), PV (FIG. 6C1; red pseudocolored from Cy5 signal), and NB (FIG. 6C2) and exhibited a fast-spiking discharge pattern (FIGS. 6E and 6F) typical of PV-expressing interneurons. The cell in FIG. 6G colabels for GFP (FIG. 6H), somatostatin (SST, FIG. 6H1; red pseudocolored from Cy5 signal), and NB (FIG. 6H2) and exhibited a rebound, adapting, non-fast-spiking pattern (FIGS. 6I-6K) typical of many SST-expressing interneurons. Scale bars: FIGS. 6B, 6G, 20 μm.

Figures 7A, 7B, 7C, 7D, 7E, 7F, 7G, 7H, 7I, 7J, 7K, 7L:
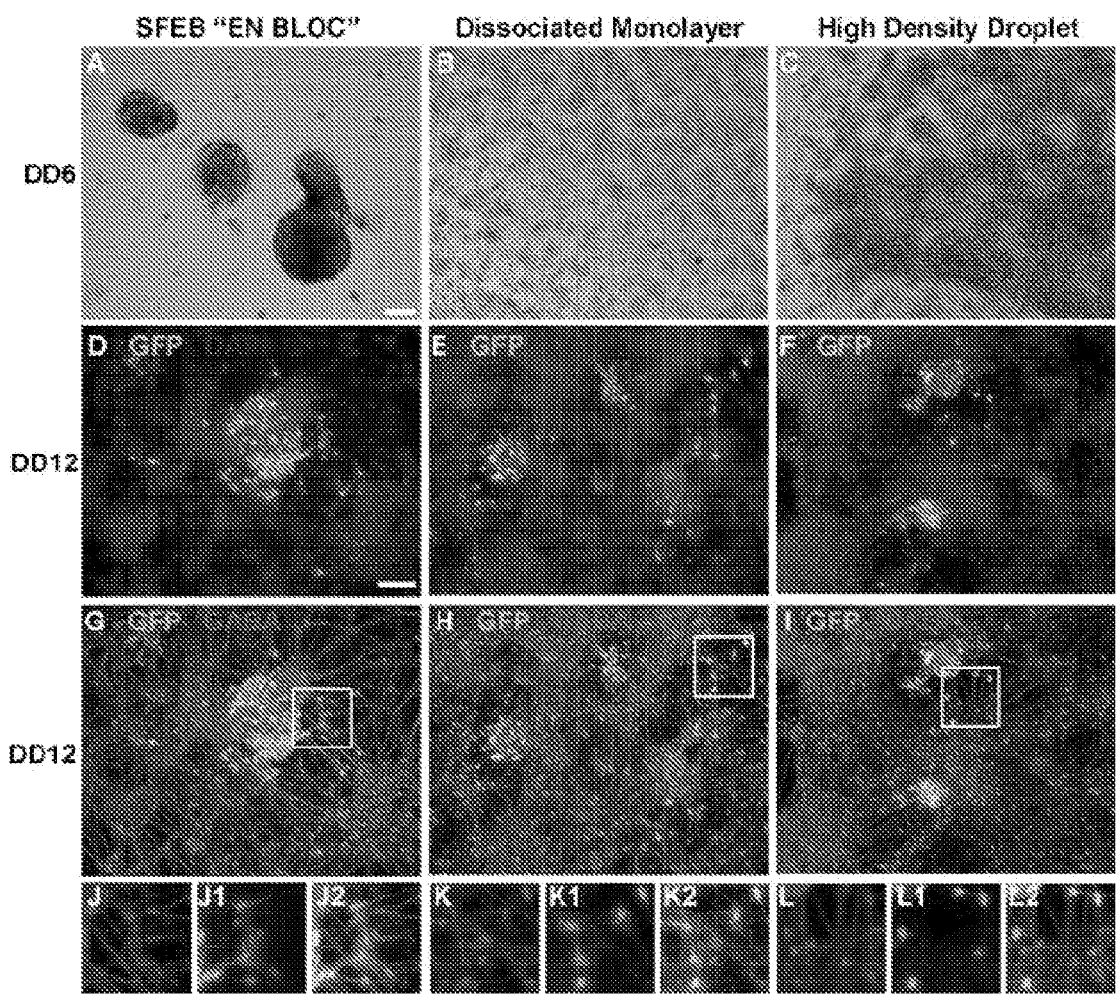
FIGS. 7A-7L demonstrate that the three methods for cell attachment after embryoid body formation give rise to Lhx6::GFP+ cells that are a subpopulation of GABA-expressing cells. On dd5, embryoid bodies were either directly plated onto an attachable substrate "en bloc" (FIGS. 7A, 7D, 7G, and 7J), or dissociated and plated as a high density monolayer (FIGS. 7B, 7E, 7H, and 7K), or dissociated and plated as high density droplets (the approach described in the Examples herein, FIGS. 7C, 7F, 7I, and 7L). By dd12, many of the cells aggregate into dense clusters with GABAergic neuronal processes as shown in FIGS. 7D-7I.

All three protocols generated Lhx6-GFP+ cells, and these GFP+ cells generally colabeled with GABA as shown in FIGS. 7J-7L2. However, the large majority of GABA+ cells do not express Lhx6-GFP. Since most of the Lhx6+ cells labeled by anti-Lhx6 immunofluorescence also have detectable Lhx6-GFP signal (FIGS. 1F, 1F1), these results suggest that the majority of GABA+ cells in these cultures are not of Lhx6+ lineages. Scale bar=200 um.

Figures 8A, 8B:
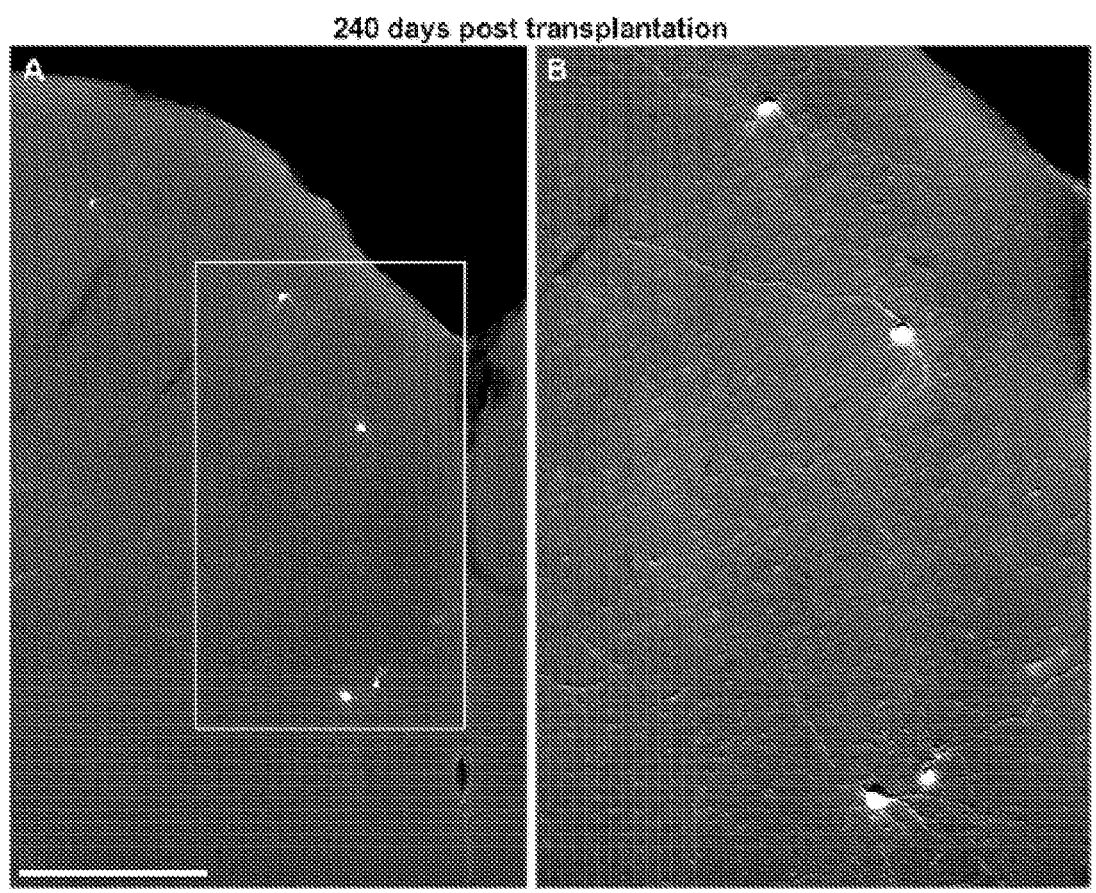

FIGS. 8A-8B show the long-term survival of Lhx6::GFP+ cells following transplantation into neonatal cortex. Shown are lower (FIG. 8A) and higher (FIG. 8B; boxed region of FIG. 8A, generated by collapsing a Z-stack of 10× images using metamorph software) magnification views of Lhx6::GFP+ cells 240 days after transplantation. The cells were labeled by GFP immunofluorescence. These GFP+ cells exhibit morphologies characteristic of mature interneurons. Scale bar=500 μm.

Figures 9A, 9B, 9C:
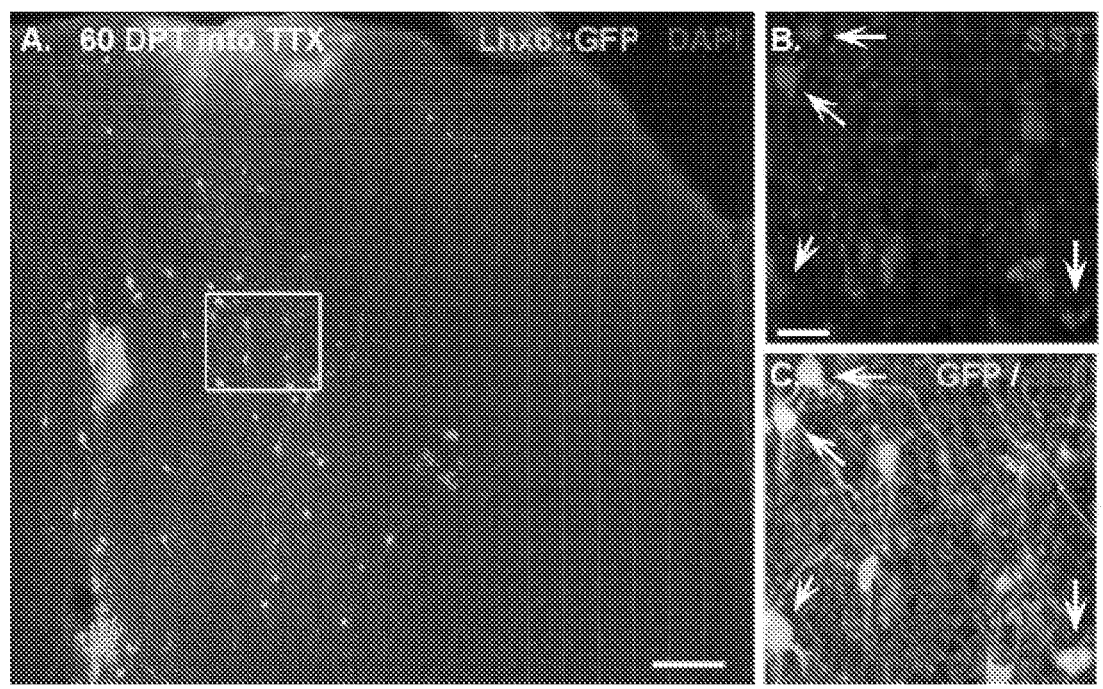

FIGS. 9A-9C show mouse ESC-derived, Lhx6::GFP+ cells differentiating into interneurons after transplantation in the mouse epileptic adult cortex. Shown are two views of a 50 ml section with immunofluorescence labeling of sorted Lhx6::GFP+ cells transplanted into the adult mouse somatosensory cortex (S1). In this experiment the animal received a small tetanus toxin (TTX) injection into S1 at 8 weeks of age, and epileptiform activity was confirmed by EEG. Six weeks later, about 30000 FACS-collected mouse ESC-derived, Lhx6::GFP+ cells were transplanted through the same burr hole used for the TTX. Sixty days after transplantation the mouse was perfused and the brain was sectioned. FIG. 9A is a lower magnification view. There is a dense collection of cell material and cells at the pial surface, and scattering of cells within the brain parenchyma. FIGS. 9B and 9C each show a higher magnification view of FIG. 9A with GFP+ neuronal processes accentuated using a z-stack of images flattened with Metamorph software. Immunohistochemical analyses show that most of these cells express neurochemical markers of MGE-derived interneurons, such as somatostatin (SST; arrows). Like the MGE-derived interneuron progenitors, mouse ESC derived progenitors can differentiate and survive after transplantation into adult, epileptic cortex, suggesting that they have potential for use in a cell-based therapy for seizures. Scale bars: 100 μm in (FIG. 9A), 20 μm in (FIGS. 9B-9C).

Figures 10A, 10B, 10C, 10D, 10E, 10F, 10G:
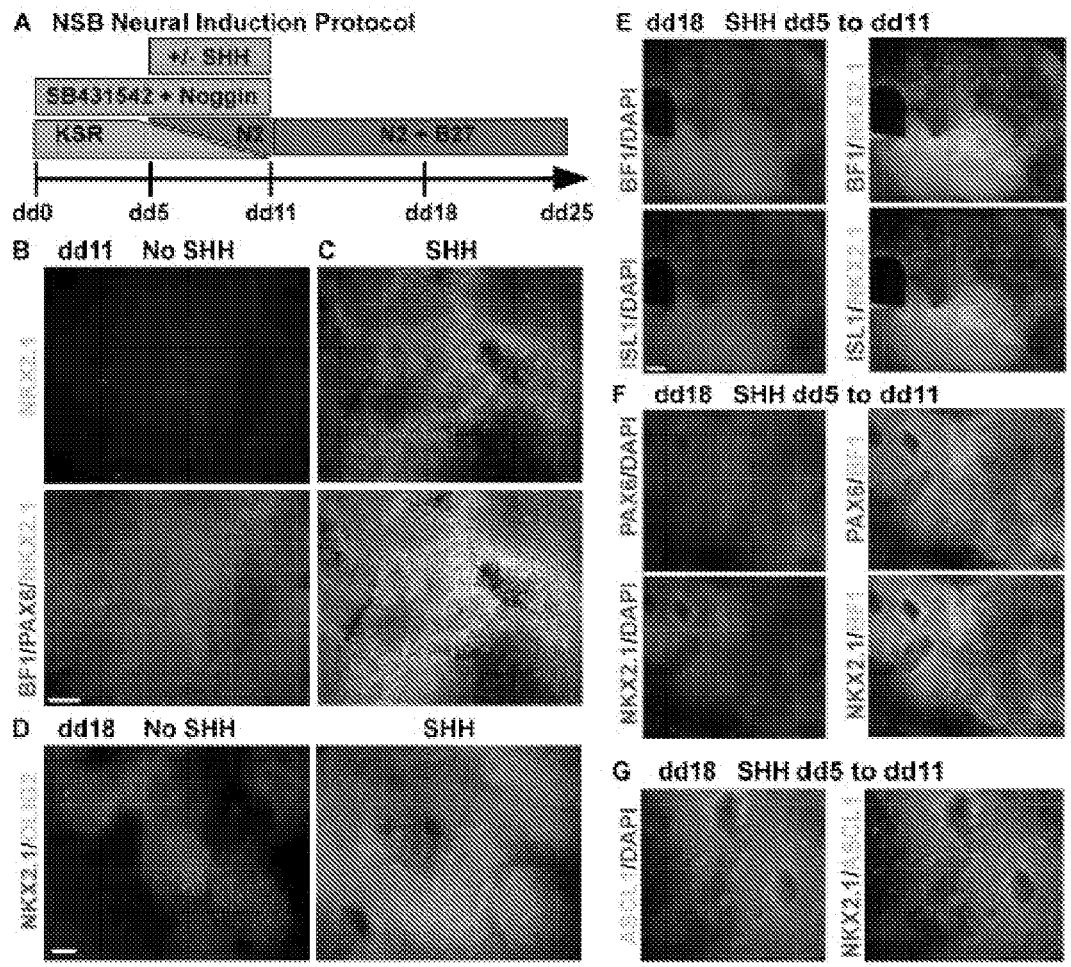

FIGS. 10A-10G demonstrate that human ES (hES) cells can be directed to rapidly differentiate into telencephalic progenitor cells characteristic of mouse-derived interneuron precursors. FIG. 10A is a schematic of the protocol used for generating pallial and subpallial progenitors from human ES cells. FIGS. 10B and 10C show fluorescent photomicrographs of hES cells differentiated with the protocol to differentiation day (dd) 11 and analyzed by immuno-fluorescence for telencephalic markers of interneuron fate. In the control group (i.e., no sonic hedgehog (shh) treatment; FIG. 10B), most of the cells enrich for Pax6 and FoxG1 (BF1). SHH treatment from dd5 to dd11 resulted in the generation of Nkx2.1+ cells, most of which co-express Pax6 and BF1 (FIG. 10C). ES cells were further differentiated with the ventral telencephalon protocol to dd18. While few of the cells differentiate into Nkx2.1+ and Olig2+ progenitors in the control group (FIG. 10D, left panel), most all of the cells treated with SHH co-expressed Nkx2.1 and Olig2, both markers of the MGE-derived interneuron precursors in mouse (FIG. 10D, right panel). Nearly all of the Nkx2.1-expressing cells also express BF1/FoxG1, and many co-express Is1-1 (FIG. 10E). As shown in FIG. 10F, by dd18, the Nkx2.1-expressing cells rarely co-label with Pax6-expressing cells, while both progenitor domains continue to express BF1/FoxG1. Many of the Nkx2.1-expressing cells also express ASCL1, a marker described to be expressed in human and primate interneuronal precursors (FIG. 10G). SHH (C25II, R&D systems) concentration was 2.5 nM, n=4. Scale bars: 100 μm in (FIGS. 10B-10C); 200 μm in (FIGS. 10D-10GG). Abbreviations: MGE, medial ganglionic eminence.

Figures 11A, 11B, 11C, 11D, 11E, 11F, 11G:
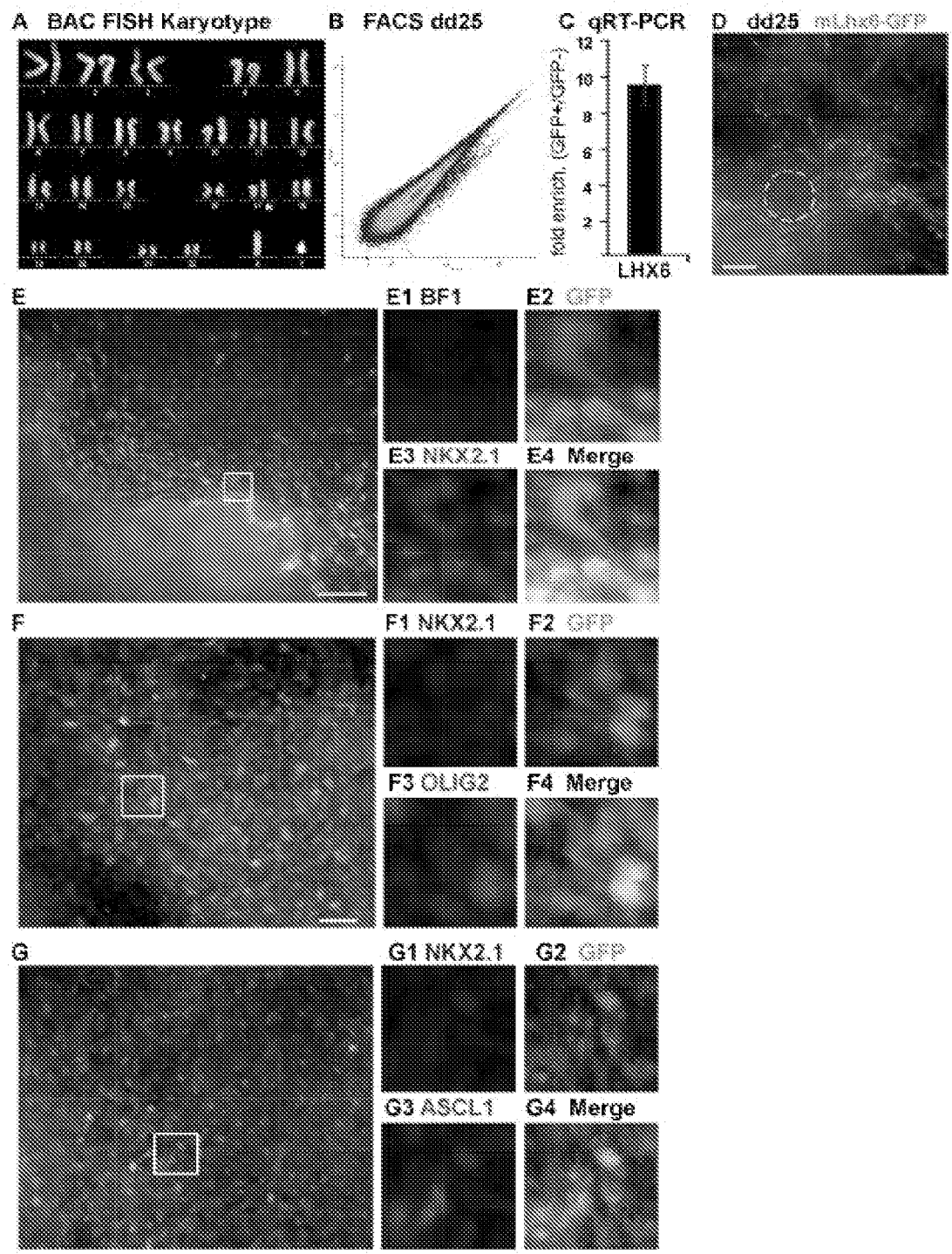

FIGS. 11A-11G illustrate the generation and characterization of the Lhx6::GFP hESC lines. The WA-09 and I6 hESC lines were nucleofected with the mouse Lhx6::GFP BAC, and screened using G418 selection and GFP expression to create the modified, stable transgenic hESC lines. Cytogenetic FISH analysis showed a normal karyotype and revealed a single BAC integration site at 17q25 (FIG. 11A; red dots), which is distinct from the endogenous Lhx6 locus at 9q33 (asterisk). The Lhx6::GFP line was differentiated to day (dd) 25 using the SHH protocol described in FIG. 10A. FACS analysis at dd25 shows a GFP+ population clearly segregating from the autofluorescent band (FIG. 11B). Quantitative RT-PCR analysis of the Lhx6 transcript shows enrichment in the sorted GFP+ cells over the GFP− cells (FIG. 11C). FIGS. 11D-11G show the immunofluorescent characterization of the Lhx6::GFP line. GFP+ cells appear on the periphery of rosette-like clusters (dotted circle) and exhibit a prominent leading process, similar to that of migrating interneuronal progenitors (FIG. 11D). Most of the GFP+ cells appear to emanate from Nkx2.1-expressing cells, and often co-express the telencephalic marker BF1/FoxG1 (FIGS. 11E-11E4), OLIG2 (FIGS. 11F-11F4), and ASCL1 (FIG. 11G-11G4) indicating that ventral-telencephalon-like progenitors are being generated. Abbreviations: BAC, bacterial artificial chromosome; FISH, fluorescence in situ hybridization; GFP, green fluorescent protein; hESC, human embryonic stem cell; qRT-PCR, quantitative reverse transcription-polymerase chain reaction. Scale bar: 20 μm in (FIGS. 11D-11G4).

Figures 12A, 12B, 12C, 12D, 12E, 12F, 12G, 12H, 12I:
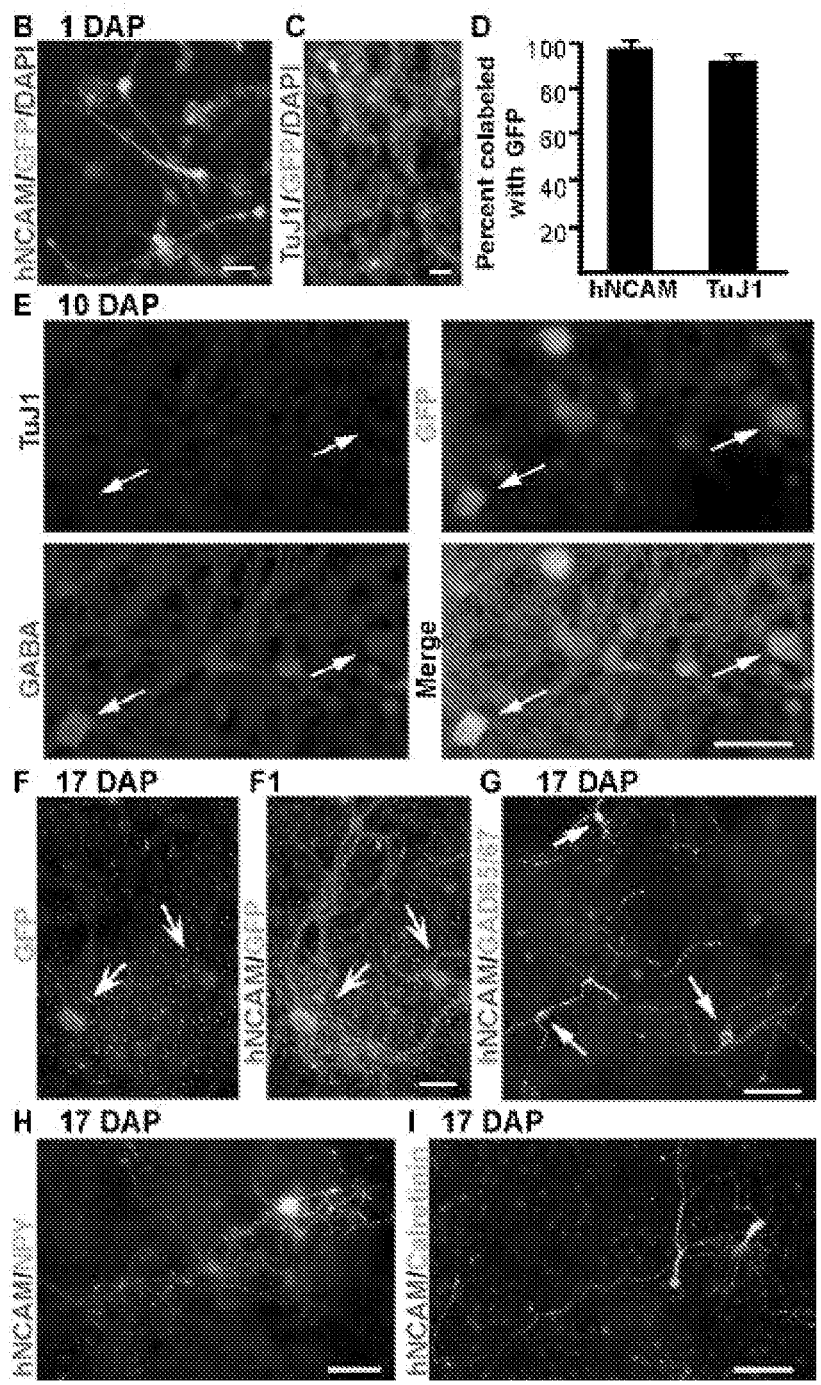

FIGS. 12A-12I depict the maturation of hESC-derived Lhx6::GFP+ progenitors into distinct groups of interneuron-like cells when cultured in an in vitro cortical environment. As shown in FIG. 12A, Lhx6::GFP+ cells were differentiated for 32 days, collected by FACS, and plated onto an E13.5 mouse neocortical feeder culture that was generated 7 days prior. FIGS. 12B-12F1 are photomicrographs showing fluorescent immunolabeling of GFP+ cells with various neuronal markers. One day after plating (DAP), the GFP+ cells co-label for human neural cell adhesion molecule (hNCAM) (FIGS. 12B and 12D), express neuronal markers (TuJ1) (FIGS. 12C and 12D), and exhibit a morphology suggestive of migrating neurons. GFP+ cells did not colabel with GFAP. At 10 DAP, many of the GFP+ cells colabel with the neurotransmitter GABA and TuJ1 (FIG. 12E). At 17 DAP, since the GFP detection was weak (FIG. 12F) and hNCAM consistently labeled the morphology of the human derived cells, hNCAM was used to label human progenitors in FIGS. 12G-12I. All markers in green were pseudocolored from Cy5. Many of the hNCAM+ neurons expressed the inhibitory enzymes GAD65 and GAD67 (FIG. 12G). A few of these hNCAM+ cells expressed the interneuron markers neuropeptide Y (NPY; FIG. 12H) or calretinin (FIG. 12I). Scale bars: 20 μm in (FIGS. 12C, 12E, 12G-12I); 10 μm in (12B, 12F)

Figures 13A, 13B, 13C, 13D, 13E, 13F, 13G:
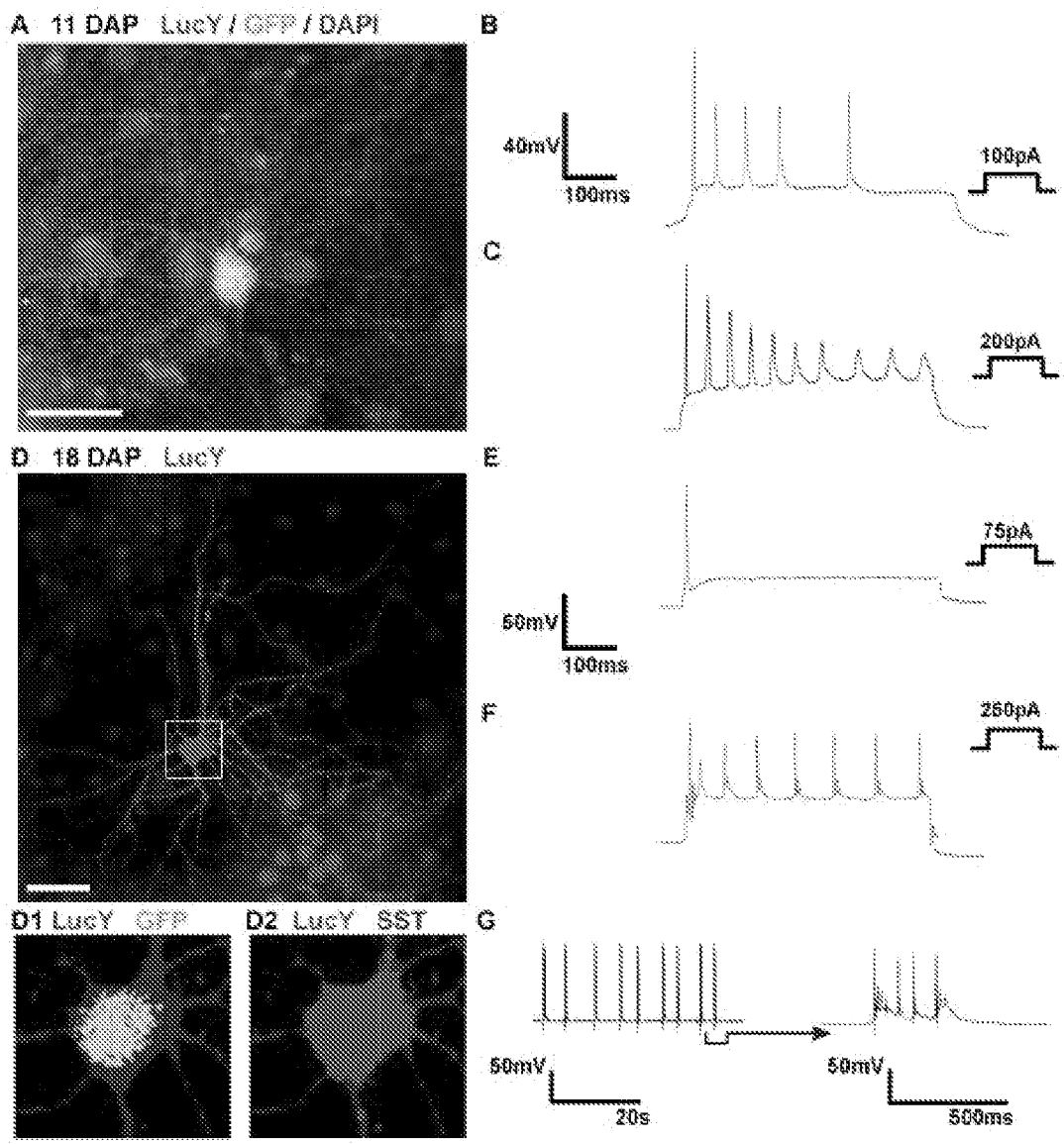

FIGS. 13A-13G show hESC-derived, Lhx6::GFP+ cells exhibit physiological and neurochemical characteristics of cortical interneurons. Sorted GFP+ cells were plated onto glass coverslips with cortical feeders and subjected to whole-cell patch clamp and filled with lucifer yellow (LucY; red signal from anti-LucY immunofluorescence). Immunolabeling of a GFP+ cell recorded at 11 DAP showed GFP expression with LucY (FIG. 13A), but no expression of an interneuron marker. When this cell was subjected to electrophysiological recordings, it elicited action potentials at 1× threshold (FIG. 13B), but failed to maintain a consistent firing pattern at 2× threshold (FIG. 13C), suggesting that this cell was an immature neuron. FIGS. 13D-13G show the collapsed stack from confocal images of a GFP+ (FIG. 13D1) cell recorded after 18 days in culture. This cell also expresses the interneuron subgroup marker somatostatin (SST; blue signal pseudocolored from Cy5, FIG. 13D2) together with LucY (FIG. 13D). When subjected to current injections, this cell elicited an action potential at 1× threshold (FIG. 13E), and showed a regular spiking, non-accommodating firing response to depolarization at 3× threshold (FIG. 13F), a pattern seen in some SST+ interneurons. Spontaneous, intrinsic burst spiking activity was observed in this cell when voltage-clamped at 0 mV as shown in FIG. 13G. Scale bar: 20 μm in (FIGS. 13A, 13D).

Figures 14A, 14B, 14C, 14D, 14E, 14F, 14G:
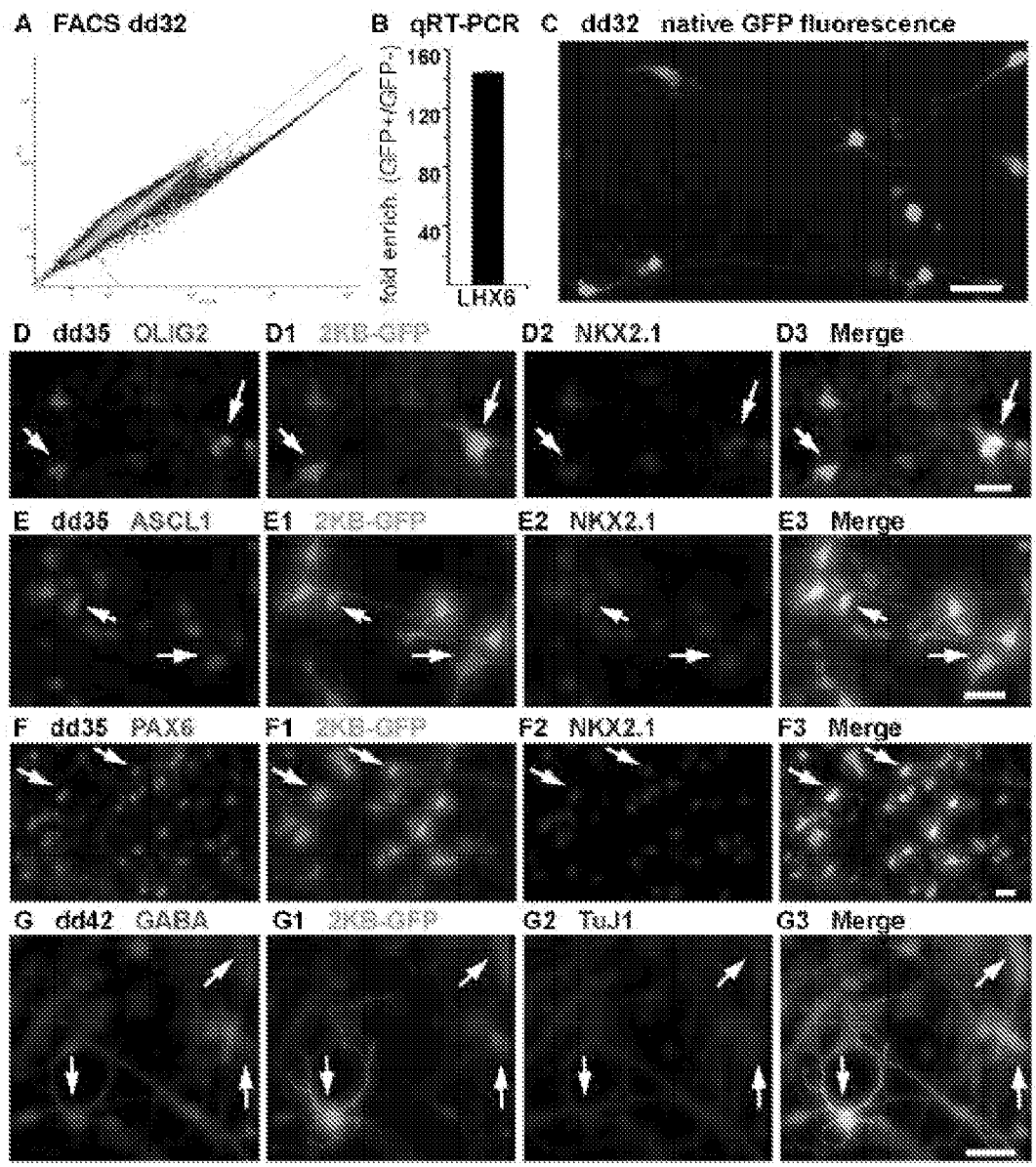

FIGS. 14A-14G demonstrate iPSC differentiation to Lhx6::GFP-expressing, GABAergic neuronal progenitors. iPS-14 was generated and screened for pluripotency markers (Papapetrou et al., "Stoichiometric and Temporal Requirements of Oct4, Sox2, Klf4, and c-Myc Expression for Efficient Human iPSC Induction and Differentiation," *Proc. Natl. Acad. Sci. USA* 106:12759-12764 (2009), which is hereby incorporated by reference in its entirety). After 25 days of differentiation following the SHH protocol, the human iPSC-derived progenitors were dissociated to single cells, nucleofected (Amaxa) with a construct expressing GFP under the control of a 2 kb mouse Lhx6 promoter region (Du et al., "NKX2.1 Specifies Cortical Interneuron Fate by Activating Lhx6," *Development* 135:1559-1567 (2008), which is hereby incorporated by reference in its entirety), and analyzed 7 days thereafter (dd32). FACS analysis revealed a clear GFP band segregating from the autofluorescent band (FIG. 14A). qRT-PCR analysis shows enrichment of the Lhx6 transcript in the sorted GFP+ cells over the GFP− cells (FIG. 14B). Through native fluorescent protein expression, many of the GFP+ cells appear to have neuronal morphologies with growth cone processes (FIG. 14C). FIGS. 14D-14G3 show the immunofluorescent characterization of Lhx6::GFP+ cells. Many of the GFP+ cells consistently co-label with the ventral telencephalic markers Nkx2.1 (FIGS. 14D1-14D3 and 14E1-14E3), OLIG2 (FIGS. 14D and 14D3), and ASCL1 (FIGS. 14E and 14E3), suggesting that interneuronal progenitors are being generated and labeled by GFP, consistent with the Lhx6::GFP BAC reporter. Unlike in rodents, the dorsal telencephalic marker, Pax6, and Nkx2.1 are often co-expressed in the GFP+ cells (FIGS. 14F-14F3). After another week in culture (dd42) and two weeks after nucleofection, the GFP+ cells are GABA-expressing neurons (TuJ1) (FIGS. 14G-14G3). Abbreviations: hIPSCs, human induced pluripotent stem cells; qRT-PCR, quantitative reverse transcription-polymerase chain reaction. Scale bar: 20 μm in (FIGS. 14C-14G3).

DETAILED DESCRIPTION OF THE INVENTION

A first aspect of the present invention relates to a method of isolating an enriched or purified population of mammalian cortical or striatal immature interneuron precursor cells from an isolated population of cells. This method involves providing an isolated population of cells and selecting a promoter and/or enhancer region which specifically functions in cortical or striatal immature interneuron precursor cells, but not the isolated population of cells. The method further involves introducing a nucleic acid molecule encoding a marker protein under control of the promoter or enhancer region into the isolated population of cells and inducing production of cortical or striatal immature interneuron precursor cells from the isolated population of cells. The cortical or striatal immature interneuron precursor cells are allowed to express the marker protein, and the cells expressing the marker protein are separated from the induced isolated population of cells, thereby isolating an enriched or purified population of cortical or striatal immature interneuron precursor cells.

The enriched or purified population of mammalian cortical or striatal immature interneuron precursor cells that are isolated in accordance with the method of the present invention encompass a population of cells that are committed to an interneuron fate (i.e., they are not pluripotent or multipotent cells). This enriched or purified population is characterized by its expression of Lhx6. In a preferred embodiment of the invention, >85% of the cells in the enriched or purified preparation express Lhx6, more preferably, >95% of the cells express Lhx6, and most preferably, >99% of the cells express Lhx6.

In accordance with this aspect of the invention the enriched or purified population of mammalian cortical or striatal immature interneuron precursor cells can be isolated from a population of stem cells. As used herein, the term "stem cells" encompasses any cell having the ability to proliferate and form a cell of more than one different phenotype. Stem cells are further capable of self renewal, either as part of the same culture or when cultured under different conditions. Stem cells suitable for use in the methods of the present invention include embryonic stem cells or germ cells, adult stem cells, and induced pluripotent stem cells. In a preferred embodiment, the stem cells are human stem cells.

Embryonic stem ("ES") cells include any multi- or pluripotent stem cell derived from pre-embryonic, embryonic, or fetal tissue at any time after fertilization, and have the characteristic of being capable under appropriate conditions of producing progeny of several different cell types that are derivatives of all three germinal layers (endoderm, mesoderm, and ectoderm), according to a standard art accepted test (e.g., the ability to form a teratoma in 8-12 week old SCID mice). In a preferred embodiment of the present invention, the stem cells are mammalian embryonic stem cells. More preferably, the embryonic stem cells of the present invention are human embryonic stem cells.

Methods for culturing embryonic stems cells, particularly human embryonic stem cells, are known in the art and described in WO2006/029297, WO2006/019366 and WO2006/029198 all to Thomson and Ludwig, and WO2008/089351 to Bergendahl and Thomson, which are hereby incorporated by reference in their entirety.

Embryonic germ ("EG") cells are derived from primordial germ cells and exhibit an embryonic pluripotent cell phenotype. EG cells are capable of differentiation into cells of ectodermal, endodermal, and mesodermal germ layers. EG cells can also be characterized by the presence or absence of markers associated with specific epitope sites. Methods for isolating, culturing, and characterizing human EG cells are described in Shamblott et al., "Human Embryonic Germ Cell Derivatives Express a Broad Range of Developmentally Distinct Markers and Proliferate Extensively In Vitro," *Proc Natl Acad Sci USA* 98(1):113-118 (2001), which is hereby incorporated by reference in its entirety.

Adult stem cells, as used in accordance with the present invention, encompass cells that are derived from any adult tissue or organ that replicate as undifferentiated cells and have the potential to differentiate into at least one, preferably multiple, cell lineages. General methods for producing and culturing populations of adult stem cells suitable for use in the present invention are described in WO2006/110806 to Xu et al., WO2002/057430 to Escoms et al., and WO2006/112365 to Nagaya, which are hereby incorporated by reference in their entirety.

Induced pluripotent stem cells ("iPSC"), preferably human iPSCs, are also suitable for use in the methods of the present invention. iPSCs, as used herein, refer to pluripotent stem cells induced from somatic cells, e.g., a population of differentiated somatic cells (see e.g., Takahashi et al., "Induction of Pluripotent Stem Cells From Adult Human Fibroblasts By Defined Factors," *Cell* 131(5):861-872 (2007); Park et al., "Reprogramming of Human Somatic Cells to Pluripotency With Defined Factors," *Nature* (2007); and Yu et al., "Induced Pluripotent Stem Cell Lines Derived From Human Somatic Cells," *Science* 318(5858):1917-1920 (2007), which are hereby incorporated by reference in their entirety). iPSCs are capable of self-renewal and differentiation into cell fate-committed stem cells, including various types of mature cells. iPSCs exhibit normal morphological (i.e., round shape, large nucleoli and scant cytoplasm) and growth properties, and express pluripotent cell-specific markers (e.g., Oct-4, SSEA-3, SSEA-4, Tra-1-60, Tra-1-81, but not SSEA-I). iPSCs are substantially genetically identical to their respective differentiated somatic cells of origin, yet display characteristics similar to higher potency cells, such as ES cells. iPSCs can be obtained from various differentiated (i.e., non-pluripotent and multipotent) somatic cells. Although various somatic cells are suitable for iPSC induction, higher reprogramming frequencies are observed when the starting somatic cells have a doubling time of about twenty-four hours. Somatic cells useful for carrying out the methods of the present invention include non-embryonic cells obtained from a fetal, newborn, juvenile or adult primates. Preferably, the somatic cells are human somatic cells. Examples of somatic cells include, but are not limited to, bone marrow cells, epithelial cells, fibroblast cells, hematopoietic cells, hepatic cells, intestinal cells, mesenchymal cells, myeloid precursor cells and spleen cells. Other somatic cells suitable for use in the present invention include CD29$^+$ CD44$^+$ CD166$^+$ CD105$^+$ CD73$^+$ and CD31$^+$ mesenchymal cells that attach to a substrate. Alternatively, the somatic cells can be cells that themselves proliferate and differentiate into other types of cells, including blood stem cells, muscle/bone stem cells, brain stem cells, and liver stem cells. Multipotent hematopoietic cells, including myeloid precursor or mesenchymal cells, are also suitable for use in the methods of the invention. Methods for producing and culturing populations of iPSCs are described in WO2008/118820 to Thomson and Yu and WO2007/069666 to Yamanaka, which are hereby incorporated by reference in their entirety.

In another embodiment of this aspect of the present invention the population of cells is a population of neural progenitor or neural precursor cells, preferably a population of human neural progenitor or neural precursor cells. Neural progenitor or neural precursor cells encompass cells that can generate progeny that are either neuronal cells (such as neuronal precursors or mature neurons) or glia cells (such as glial precursors, mature astrocytes, or mature oligodendrocytes). Typically, the cells express some of the phenotypic markers that are characteristic of the neural lineage (e.g., A2B5), and they do not produce progeny of other embryonic germ layers when cultured by themselves in vitro, unless dedifferentiated or reprogrammed in some fashion.

In yet another embodiment of this aspect of the present invention, the population of cells is a population of transdifferentiated cells, preferably a population of human transdifferentiated cells. Transdifferentiated cells encompass mature differentiated cells of one tissue type whose phenotype is transdifferentiated or redirected into the phenotype of a mature cell of a different tissue without necessarily reverting to a pluripotent or multipotent phenotype. Cells that can undergo transdifferentiation include any somatic cell as well as adult stem cells. Methods of transdifferentiating cells are known in the art (see e.g., Thomas Kuntziger and Philippe Collas, *Transdifferentiation*, in HANDBOOK OF STEM CELLS 147 (Robert Lanza ed., 2004), which is hereby incorporated by reference in its entirety). Methods of producing transdifferentiated neural progenitor cells and neuronal progenitor cells are described in U.S. Pat. Nos. 6,949,380, 6,087,168, and 7,041507 to Levesque et al., and U.S. Patent Publication Nos. 20060099190 to Suh et al. and 2006/0251624 to Dezawa, which are hereby incorporated by reference in their entirety).

The promoter and/or enhancer region used in accordance with this aspect of the present invention, is one that specifically functions in cortical or striatal immature interneuron precursor cells and does not function in other cell types. It is chosen to selectively drive the expression of a marker protein in immature interneuron precursor cells derived from the population of stem, progenitor, or transdifferentiated cells. Any promoter which is specific for cortical or striatal immature interneuron precursor cells can be utilized in this process.

In one embodiment of the present invention, the selected promoter and/or enhancer region comprises a 5' untranslated and/or translated region of the Lhx6 gene. Lhx6 is a homeodomain-containing transcription factor that is expressed in medial ganglionic eminence (MGE) derived interneurons from the time of cell cycle exit (Lavdas et al., "The Medial Ganglionic Eminence Gives Rise to a Population of Early Neurons in the Developing Cerebral Cortex," *J Neurosci* 19(18):7881 (1999), which is hereby incorporated by reference in its entirety) through postnatal maturation (Cobos et al., "Mice Lacking Dlx1 Show Subtype-Specific Loss of Interneurons, Reduced Inhibition and Epilepsy," *Nat Neurosci* 8(8):1059 (2005), Fogarty et al., "Spatial Genetic Patterning of the Embryonic Neuroepithelium Generates GABAergic Interneuron Diversity in the Adult Cortex," *J Neurosci* 27(41):10935 (2007), and Liodis et al., "Lhx6 Activity is Required for the Normal Migration and Specification of Cortical Interneuron Subtypes," *J Neurosci* 27(12):3078 (2007), which are hereby incorporated by reference in their entirety). Lhx6 is a direct target of the transcription factor Nkx2.1 and is critical to the specification of parvalbumin and somatostatin expressing interneurons. In a preferred embodiment, the Lhx6 promoter and/or enhancer regions comprises at least one or more conserved Nkx.2 binding regions. One such conserved Nkx.2 binding region comprises SEQ ID NO:3 as shown below and disclosed by Du et al., "Nkx2.1 Specifies Cortical Interneuron Fate by Activating Lhx6," *Development* 135:1559-67 (2008), which is hereby incorporated by reference in its entirety.

```
                                          (SEQ ID NO: 3)
   cttgattcgc taatgaagtt ctcggtgccc aa      32
```

As described herein, an exemplary Lhx6 promoter and/or enhancer region comprises the 2 kb fragment derived from the mouse Lhx6 gene promoter/enhance region having a nucleotide sequence of SEQ ID NO:1 shown below.

```
cagcctttag aagctggtgc aagctccggt tgtcatgaag cagggatatt tttgcaggag    60
tttgagggggt gtgtcgaagt ctaggacctg aaggattggt gtgagcaggt gaccatttgc   120
gacacaaata taccaggctc agcactacat aacagaacg tggcttcatg tggaatccag    180
ccttgtagat gggctgacca cggattcctc tcgcacctat taacgttgtg tgagggcggc   240
agtgggtgcc cttgagggag gggcggcaga aggagctgtg aggatatgtg ccccgccagt   300
gtctttgtat gttagcatgt tccaagagtc tccctgtagc gcctagtttc agtgtgtctc   360
tctgtgtgtg tatgtctctg agtctctgcc tcctttggag tgtctcgctc ttcttagcgg   420
ggagggggatt ggtcacgcat gactcatctt gaacggagcg gggctccagc ggcagggcgg   480
tcgtcgccgc agctggaagg ggaggaggac aacgaggagg gagaacagga ggaggaagag   540
gaggaggagg aagaggagga ggaggcggca gccgcagaag cagctgcagg gacctctcca   600
agtttgtcgg gaccttcttc agaggcagtg gtgctggcag ccagggaggc caggactgcg   660
ctcaggccgg gggcggggag ctggggctgg gcccggggcg gcggggccgg agcctcggtt   720
ctccagctct cccagcagcc tctgccccca ggacgcccga ggccccactc tgcgcctctc   780
ttcgcactgc gcgcccaccg agccctcccg ctcccgggcc catgtactgg aagcatgaga   840
gcgccgcccc ggcgctgccc gagggctgcc ggttgccggc ggagggcggc cccaccaccg   900
accaggtgag caagcaggcg agtgggtgag cgtcggggat cctgggccag cgggagccg   960
ggattcaacc gggccgggtc gggtggcggg cggcagcagg aaggagggggt gctgagtgag  1020
cccgggagag tgtgtctgca agtgtgtgag cgtgcgagcg ggcaggcggg ggtgggggt   1080
cgcggaaagc gggaacacat tatgcaaatg ttggaggaat ttctcaaaaa gcgatttagc  1140
aaagacatag gcgaatcaag aggaggcgag gccagtattg tccgtctgaa tagacgctga  1200
tagcgccgat gcgccagagg ttgtgccggc gcaacgctga ggatctcgat gaggggccgg  1260
tcccgggagc tccaagagtc tggagggttc tctttcctcc tccaagaggc ctctcttttc  1320
tcttttggc ctcatttcac tcgccgatct cgccctcttt ggcttgggc ttcccttgaa  1380
ctggccctcc aaaggcgttt gaatcggtgt caatatcccc gcttcaattt cccggcgcgc  1440
gtcgagcggg cggatgctcc tagcgctctg ggttttattt tctcaaccac caccaccact  1500
accaccacca ccaccccccat ctccttttta ttttctttct ttctctcttt tctccttttt  1560
gcatttgta ccgagagtag gagaagggag ggggcggagg gagaaaaaaa ttcgattttt  1620
aattactacc attaaaaaat caaatttgca attctttggg cggcctgatg gatctcactg  1680
attgacagtt ggaattgaca ctctggctac ctcttatctt gggcattcac gacaatttct  1740
aattgcaggt agtttgtgtg tgtgcgcgtg tttttttcc ccctcagagg cttggattgc  1800
aaaggaacta agcgattact tcaagagcca cgggttaagt gcaggagag ggggagagag  1860
agggaaaaaa acccaatcca aattcaaatt gcttcattag agagacaccg cttttgtggg  1920
gaagggcttt aaatgcccac tacaaagtta ggactcattg ttcagcgccg gtttatataa  1980
caggcgaggg gaggcgctgg gctctgacag ctccgagcca gttcagcagc cgccgtcgcc  2040
tgcattccct cccctcccc caggtgatgg cccagccagg g                       2081
```

Alternatively, the Lhx6 promoter and/or enhancer region comprises the corresponding 2 kb fragment derived from the human Lhx6 gene having a nucleotide sequence of SEQ ID NO:2 as shown below.

```
gaaggggggct gagactctaa gtgtccactt gtgtatgctg cagggcgtta gtgtgtgtaa    60
ggctccatct ttgggtttga aggttctgtg tctgtgtgtc tggggggcagt gtcttctgtc  120
```

-continued

```
taaatgcctg ggccttcctg ccttcccctac cattctcatt gtcagtagaa ccctagagaa      180
gaagggatgg gcattggact gtgtggttaa gcaaatcctg aagggaaggg gaatgtgcca      240
agcaatccct tccaagagaa ttcagggaaa ctaccctccc gtttcacctc agtccctggg      300
agctggtgca ctgtctggtt cttatagagc agaggtatct gtgcaggtgt gtgagagtaa      360
gtgtggtgcc tcgtgcccgt gtaaatgatg tgaacaggta atcacttaca ttagtgtgta      420
cacaaatgta ccaggcatgg gattgcatca acacagtgta ataacgtgtg acctcctacg      480
gaatctatct ccgcagatgg tatggccatg ggtccctcct gtacctgtga gtggggcagt      540
gtctgaggaa gatgggtgcc ccttgaggga ggagcggtag tgagagctgg gtggatgtgt      600
gcccgccggt gcctttgtgt actggcgtgt ctccgagtct ctctgtcggc agctctgagt      660
ttctgtgtgt ctctgtgtct gtgtgtgtgt ctctctctct gggtctctgc ctcgtcgtgt      720
gtgtcttgct ctcccttggc ggggagggga ttggtcacgc atgactcatc ttgaaccgag      780
cggggctcca gcggcagggc ggccgccgtt gcagctggag ggggaggagg acaaggagga      840
gggagaggag gaggaggact accaagaggg ggaggaggag aagaaggagg gggcggggc      900 ctctccaagt ttgtcgggac cttcttccga ggcagcggcg gcagcagcca gggaggccgg      960
ggctgcgcgc gggccggggg cggggctga ggccgggccc ggggcggcgg ggccggcgcc     1020
tcggctctcc tcctgctcct gcagcagcct ctgctcccac tgcggctgtg gtcccctcg     1080 gcgcagctct ccgcgctgcg cgcccgctga gcccgaggtt ccccggccca tgtactggaa     1140
gcatgagaac gccgccccgg cgttgcccga gggctgccgg ctgccggccg agggcggccc     1200
cgccaccgac caggtgagcc ggcgaacgac tgggtgagcg gcccgggccg gggtcgggca     1260
gggtccggga cccagccggg ccgagcaggg tggcgggcgg ttgcaggaag gaggggtacg     1320
agggtgcgcg tgtgagtgtg tgcttgtgag tgtgggagcg cgcgcgcgag cggggggggg     1380
gggtcgcgga aagcgggaac acattatgca aatgttggag gaatttctca aaaagcgatt     1440
tagtaaagac acaggcgaat caagaggagg cgaggccggt attgtccgtc tgaataggcg     1500
ctgatagcgc cgatgcgccg ggggttgtgc cggcgcagcc ctgagaatcc cgacgcgggg     1560
ccggtacccg gcgcgccgag gggctggagg gtgcttttc ctccccttga gcgcctctct     1620
tttctctttt tggtcccgtt tcgccccgat ctcgctctct ttttgctccg ggtttccctc     1680
cgactggccc tcgaaaggcg cctgaatccg tgtcaatata gctgcttcaa tttcgccgcg     1740
cgtgtcaggc gggcgggcgg gcgggtgctc accgcgctcg gggttttctt ttcttcaacc     1800
accctccgcc cctcacccat ctctttttta ttttctttct ttctctcttt tctcctttt     1860 gcattttgtg ccgagaggag aagggagcga ggaagggag tggggtgggg gggcgggtgg     1920
agagagaaaa aattcgattt ttaattacta ccattaaaaa atcaaatttg caattctttg     1980
ggcggcctga tggatctcac tgattgacag ttggaattga cactctggct acctcttatc     2040
ttgggcattc acgacaattt ctaattgcag gtagtttgtg tgtgtgtgcg cgtgtttttc     2100
ttcccccctc agaggcttgg attgcaaggg aactaagcga ttacttcaag agccacgggt     2160
taagtgcagg gagaggggga gagagaggga aaaaatccaa tccaaattca aattgcttca     2220
ttagagagac accgcttttg tggggaaggg ctttaaatgc ccactacaaa gttaggactc     2280
attgttcggc gccggtttat ataacaggcg cggggaggcg ctgggctcag gctgtgcgga     2340
gccagttcag cagccgccgc cgcctgcgtt ccctcccccc ctcccccagg tgatggcc      2398
```

In an alternative embodiment of this aspect of the present invention, the promoter and/or enhancer region that specifically functions in cortical or striatal immature interneuron precursor cells comprises an Nkx2.1 promoter or enhancer region. Suitable promoter and enhancer regions of the Nkx2.1 gene are known in the art (see e.g., Xu et al., "Fate Mapping Nkx2.1-Lineage Cells in the Mouse Telencephalon," *J Comp Neurol* 506(1):16-29 (2008), which is hereby incorporated by reference in its entirety).

In accordance with this aspect of the present invention, a suitable marker protein is any protein that allows for the easy identification and separation of the cells in which it is expressed, in this case the cortical or striatal immature interneuron precursor cells. Suitable marker proteins include any of the commonly used fluorescent and luminescent reporter or marker proteins known in the art. As described in the Examples herein, the marker protein can be a green fluorescent protein (GFP). The isolated nucleic acid molecule encoding the green fluorescent protein can be deoxyribonucleic acid (DNA) or ribonucleic acid (RNA, including messenger RNA or mRNA), genomic or recombinant, biologically isolated or synthetic. In one embodiment, the GFP is derived from *Aequorea victoria* (U.S. Pat. No. 5,491,084 to Chalfie et al., which is hereby incorporated in its entirety). A mutated form of this GFP (a red-shifted mutant form) designated pRSGFP-C1 is commercially available from Clontech Laboratories, Inc. (Palo Alto, Calif.).

Mutated forms of GFP that emit more strongly than the native protein, as well as forms of GFP amenable to stable translation in higher vertebrates, are now available and can be used for the same purpose. Alternatively, the GFP can be in humanized form (GFPh) (Levy et al., "Retroviral Transfer and Expression of a Humanized, Red-Shifted Green Fluorescent Protein Gene into Human Tumor Cells," *Nature Biotechnol.* 14:610 614 (1996), which is hereby incorporated in its entirety). Any nucleic acid molecule encoding a fluorescent form of GFP can be used in accordance with the subject invention. Cells encoding a fluorescent marker protein can be separated and isolated using fluorescent activated cell sorting (FACS) as described herein.

Other suitable marker proteins include lacZ/beta-galactosidase, luciferase, or alkaline phosphatase.

Standard techniques of molecular cloning are used to place the nucleic acid molecule encoding GFP under the control of the chosen cell specific promoter. Generally, this involves the use of restriction enzymes and ligation. The resulting construct, which comprises the nucleic acid molecule encoding the GFP under the control of the selected promoter (itself a nucleic acid molecule) (with other suitable regulatory elements if desired), is then introduced into a plurality of cells which are to be sorted. Techniques for introducing the nucleic acid molecules of the construct into the plurality of cells may involve the use of a vector which comprise the nucleic acid molecules. Suitable vectors include plasmid vectors, such as bacterial artificial chromosome, yeast artificial chromosome, and human artificial chromosome vectors, cosmid vectors, and viral vectors, such as adenoviral vectors, adeno-associated viral vectors, retroviral vectors, herpes viral vectors, and lentiviral vectors. These vectors can then be used to introduce the nucleic acid molecules into the plurality of cells.

Various methods are known in the art for introducing or transfecting (i.e., transforming or transducing) a population of cells with the nucleic acid molecule encoding the marker protein under the control of a desired promoter/enhancer region. One approach involves microinjection, where DNA is injected directly into the nucleus of cells through fine glass needles. Alternatively, the nucleic acid molecule can be introduced using dextran incubation, in which DNA is incubated with an inert carbohydrate polymer (dextran) to which a positively charged chemical group (DEAE, for diethylaminoethyl) has been coupled. The DNA sticks to the DEAE-dextran via its negatively charged phosphate groups. These large DNA-containing particles stick in turn to the surfaces of cells, which are thought to take them in by a process known as endocytosis. Some of the DNA evades destruction in the cytoplasm of the cell and escapes to the nucleus, where it can be transcribed into RNA like any other gene in the cell. In another embodiment, the nucleic acid molecule is introduced using calcium phosphate coprecipitation, where the target cells efficiently take in DNA in the form of a precipitate with calcium phosphate. Electroporation is another means for achieving cellular transfection. Using this method, cells are placed in a solution containing DNA and subjected to a brief electrical pulse that causes holes to open transiently in their membranes. DNA enters through the holes directly into the cytoplasm, bypassing the endocytotic vesicles through which they pass in the DEAE-dextran and calcium phosphate procedures (passage through these vesicles may sometimes destroy or damage DNA). Liposomal mediated transformation is yet another suitable approach for transfecting cells with DNA. Using this method the nucleic acid molecule is incorporated into an artificial lipid vesicle, a liposome, which fuses with the cell membrane, delivering its contents directly into the cytoplasm of the target cell. Delivery of a nucleic acid molecule can also be achieved using biolistic transformation, in which DNA is absorbed to the surface of gold particles and fired into cells under high pressure using a ballistic device. Finally, viral-mediated transformation, using any of the viral vectors described above, is another approach for introducing a nucleic acid molecule into a target cell.

Depending on the method of transfection chosen and the desired duration of marker protein expression, the population of cells can be transiently (i.e., the nucleic acid does not become integrated into the genome of the target cell) or stably (i.e., the nucleic acid becomes integrated into the genome of the target cell) transfected.

Either prior to or after introducing the nucleic acid molecule encoding a marker protein under the control of a selected promoter and/or enhancer region into the desired population of cells, the population of cells is induced or differentiated into cortical or striatal immature interneuron precursor cells. Differentiation is achieved by exposing the population of cells to appropriate growth factors that promote neuralization and ventralization. During the neuralization stage the cells are exposed to a neuralization factor, such as a bone morphogenetic protein (BMP) inhibitor. Suitable BMP inhibitors include, without limitation, noggin, chordin, Cerberus, gremlin, follistatin, Dan (NBL1), and CRIM1. Small molecule inhibitors of BMPs, such as LDN-193189 (available from StemGent, Cambridge, Mass.) are also suitable for use in the methods of the present invention. Alternatively, during the neuralization stage, cells are exposed to a WNT inhibitor. Known inhibitors or antagonists of Wnt signaling include the Dickkopf proteins (e.g., Dkk-1 to Dkk-4), secreted Frizzled-related proteins (sFRP), Wnt Inhibitor Factor 1 (WIF-1) and Soggy. Small molecule inhibitors of Wnt signaling are also suitable for use.

Following the neuralization stage, cells are exposed to a ventralization factor, such a sonic hedgehog (Shh). Alternatively, the cells are exposed to an agent that mimics Shh or to an agonist of Shh. In a preferred embodiment, the cells are further exposed to an agent or agents that enhance Shh signaling (i.e., enhance ventralization). As demonstrated in the Examples herein, exposure of the cells to insulin growth factor-1 (IGF-1) significantly enhances Shh signaling and cellular differentiation.

After permitting the isolated population of cells to differentiate to immature interneuron precursor cells, a purified and enriched population of the immature interneuron precursor cells is recovered. This recovery procedure is preferably carried out by the promoter based separation procedure, as described above, utilizing an enhancer/promoter which functions only in the immature interneuron precursor cells and not other cell types. A nucleic acid molecule encoding the marker protein under control of the enhancer/promoter is introduced into the cells, the immature interneuron precursor cells are allowed to express the marker protein, and the cells expressing the marker protein are separated from the mixed population of cells, where the separated cells are the immature interneuron precursor cells. As described infra, the separated cells, representing an enriched or purified population of immature interneuron precursor cells can be transplanted into a subject (e.g., a human subject) to treat a condition mediated by the loss or dysfunction of cortical or striatal interneurons or to serve as drug delivery vehicles, delivering a therapeutic agent to a target region of the subject's brain.

Another aspect of the present invention relates to an enriched or purified preparation of mammalian cortical or striatal immature interneuron precursor cells. This enriched or purified population of immature interneuron precursor cells are characterized by their expression of Lhx6. The enriched or purified preparation of immature interneuron precursor cells of the present invention is preferably at least 90% pure, more preferably at least >95% pure, and most preferably at least >99% pure. The purity of the enriched or purified preparation can be assessed by the percentage of cells in the preparation expressing Lhx6.

The enriched or purified preparation of mammalian cortical or striatal immature interneuron precursor cells can be derived from any mammal, including without limitation, human, mouse, rat, monkey, pig, dog, horse, etc. In a preferred embodiment, the enriched or purified preparation is a human preparation.

As described supra, cells of the enriched or purified preparation of cortical or striatal immature interneuron precursor cells may express a nucleic acid molecule encoding a marker protein under control of a cortical or striatal immature interneuron precursor cell specific promoter and/or enhancer region, such as an Lhx6 or Nkx2.1 promoter region. In accordance with this embodiment, the purity of the preparation can be assessed by the percentage of cells expressing the marker protein. The cortical or striatal immature interneuron precursor cells of the preparation may be transiently or stably transfected with the nucleic acid molecule. When the cells of the preparation have been stably transformed, such cells may contain a bacterial, human, or yeast artificial chromosome (or other vector) genomically integrated therein.

The enriched or purified preparation of cortical or striatal immature interneuron precursor cells of the present invention may be engineered to express or overexpress a therapeutic agent. Suitable therapeutic agents include, without limitation, neuropeptide Y, adenosine, galanin, and GABA as described herein.

The enriched or purified preparation of cortical or striatal immature interneuron precursor cells of the present invention give rise to functional interneurons, exhibiting the morphological, neurochemical, and electrophysiological properties of mature interneurons. The immature interneuron precursor preparation can mature in vitro under controlled culture conditions mimicking their in vivo neuronal environment (e.g., cultured in the presence of feeder cells as described in the Examples herein). Alternatively, the immature interneuron precursor cells mature following transplantation and migration within the cerebral cortex of a mammalian subject (e.g., a human subject). As demonstrated herein, the immature interneuron precursor cells of the present invention migrate extensively, in a non-radial (i.e., tangential) fashion upon transplantation into the cerebral cortex. Upon migration, the cortical or striatal immature interneuron precursor cells mature into parvalbumin and Kv3.1 expressing interneurons that exhibit fast spiking action potential discharge patterns. Alternatively, the cortical or striatal immature interneuron precursor cells of the present invention mature into somatostatin expressing interneurons, exhibiting the characteristic rebound, adapting, non-fast spiking firing patterns of this sub-group of interneurons. These somatostatin expressing interneurons may further express neuropeptide Y.

The enriched or purified preparation of cortical or striatal immature interneuron precursor cells mature into interneurons having an average resting membrane potential of about −40 mV to about −70 mV. Overtime, the average resting membrane potential becomes more hyperpolarized, ranging from about −55 mV to about −70 mV.

Another aspect of the present invention relates to a method of treating a condition mediated by a deficiency or loss of cortical or striatal interneuron function in a subject. This method involves providing an enriched or purified preparation of cortical and striatal immature interneuron precursor cells and administering the enriched or purified cortical and striatal immature interneuron precursor cells to a subject under conditions effective to treat the condition mediated by the deficiency or loss or cortical or striatal interneuron function. In a preferred embodiment, a subject having a condition mediated by a deficiency or loss of cortical or striatal neuron function is selected prior to administering the precursor cells. The subject can be any mammalian subject, preferably a human subject.

Conditions suitable for treatment in accordance with this method of the present invention include, without limitation seizure disorders, such as epilepsy or infantile spasms; neuropsychiatric disorders, such as autism, schizophrenia, an anxiety disorder, and an eating disorder; neurodevelopmental disorders, such as holoprosencephaly or microcephaly; and Parkinson's disease.

Administration of the cortical or striatal immature interneuron precursor cells of the present invention to a subject in need can be carried out by implantation using conventional methods (e.g., stereotactic injection) into an appropriate site within the brain (e.g., the cerebral cortex) of the subject, depending on the particular disorder being treated. The cells can be delivered via intraparenchymal or intraventricular transplantation as described in U.S. Pat. Nos. 5,082,670 and 5,650,148 to Gage et al., and U.S. Patent Publication No. 20060141622 to Johe et al., which are hereby incorporated by reference in their entirety. Intraparenchymal transplantation can be achieved by injecting the immature interneuron precursor cells within the host brain parenchyma or by preparing a cavity by surgical means to expose the host brain parenchyma and then depositing the cell graft into the cavity. Both methods provide parenchymal apposition between the grafted cells and host brain tissue at the time of grafting, and both facilitate anatomical integration between the graft and host brain tissue. Alternatively, the graft may be placed in a ventricle, e.g., a cerebral ventricle or subdurally, e.g., on the surface of the host brain where it is separated from the host brain parenchyma by the intervening pia mater or arachnoid and pia mater. Grafting to the ventricle may be accomplished by injection of the donor cells or by growing the cells in a substrate such as 30% collagen to form a plug of solid tissue which may then be implanted into the ventricle to prevent dislocation of the graft. For subdural grafting, the cells may be injected around the surface of the brain after making a slit in the dura. This is of importance if it is required that the graft become an integral part of the host brain and to survive for the life of the host.

The cell number and concentration of cells delivered in suspension should be optimized based on factors such as the age, physiological condition, and health of the subject, the size of the area of tissue that is targeted for therapy, and the extent of the pathology. Injections may be performed using single cell suspension or small aggregates at a density ranging between about 1,000 to about 1,000,000 cells per µl.

The enriched or purified preparation of cortical or striatal immature interneuron precursor cells according to the present invention can be supplied in the form of a pharmaceutical composition, comprising an isotonic excipient prepared under sufficiently sterile conditions for human administration (see CELL THERAPY: STEM CELL TRANSPLANTATION, GENE THERAPY, AND CELLULAR IMMUNOTHERAPY (G. Morstyn & W. Sheridan eds., 1996); and E. D. BALL et al., HEMATOPOIETIC STEM CELL THERAPY (2000), which are hereby incorporated by reference in their entirety).

Another aspect of the present invention relates to a method of delivering a therapeutic agent to a subject's brain. This method involves providing the enriched or purified preparation of cortical and striatal immature interneuron precursors of the present invention, where the preparation of immature interneuron precursor cells express a therapeutic agent, and administering the precursor cells to a subject under conditions effective to deliver the therapeutic agent to the subject's brain.

In accordance with this method of the invention the enriched or purified preparation of cortical or striatal immature interneuron precursor cells are engineered to express or overexpress the therapeutic agent. The therapeutic agent can be a protein, peptide, or nucleic acid molecule (e.g., an inhibitory nucleic acid molecule). For example, the precursor cells can be engineered to overexpress neuropeptide Y (NPY), a therapeutic protein agent useful for the treatment of epilepsy, eating disorders, and anxiety, or galanin, a therapeutic protein agent useful for the treatment of epilepsy. Alternatively, the precursor cells can be engineered to overexpress adenosine or GABA, therapeutic proteins useful for the treatment of seizure disorders.

The precursor cells can also be engineered to express molecules that block cell proliferation, induce cell death, or otherwise function in a manner that limits the growth of brain tumors. Brain tumors can secrete agents, such as glial cell line-derived neurotrophic factor (GDNF), that will attract migrating Lhx6+ immature interneurons transplanted into the region of a tumor. Accordingly, the precursor cells can be engineered to overexpress a non-cleavable form of the neurotrophic factor BDNF, that can antagonize actions of cleaved BDNF and promote cell death of the brain tumor cells.

Engineering the precursor cells to express or overexpress a therapeutic agent can be achieved using recombinant expression systems that are well known in the art. Generally, the use of recombinant expression systems involves inserting the nucleic acid molecule encoding the amino acid sequence of the desired therapeutic protein or peptide into an expression system to which the molecule is heterologous (i.e., not normally present). One or more desired nucleic acid molecules encoding a therapeutic protein or peptide may be inserted into the vector. When multiple nucleic acid molecules are inserted, the multiple nucleic acid molecules may encode the same or different agents. The heterologous nucleic acid molecule is inserted into the expression system or vector in proper sense (5'→3') orientation relative to the promoter and any other 5' regulatory molecules, and correct reading frame.

The preparation of the nucleic acid constructs can be carried out using standard cloning procedures well known in the art as described by Joseph Sambrook et al., MOLECULAR CLONING: A LABORATORY MANUAL (Cold Springs Harbor 1989). U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in a suitable host cell.

A variety of genetic signals and processing events that control many levels of gene expression (e.g., DNA transcription and messenger RNA ("mRNA") translation) can be incorporated into the nucleic acid construct to maximize therapeutic protein or peptide production. For the purposes of expressing a cloned nucleic acid sequence encoding a desired peptide, it is advantageous to use strong promoters to obtain a high level of transcription. Common promoters suitable for directing expression in mammalian cells include, without limitation, SV40, MMTV, metallothionein-1, adenovirus Ela, CMV, immediate early, immunoglobulin heavy chain promoter and enhancer, and RSV-LTR.

There are other specific initiation signals required for efficient gene transcription and translation in prokaryotic cells that can be included in the nucleic acid construct to maximize protein or peptide production. Depending on the vector system and host utilized, any number of suitable transcription and/or translation elements, including constitutive, inducible, and repressible promoters, as well as minimal 5' promoter elements, enhancers or leader sequences may be used. For a review on maximizing gene expression see Roberts and Lauer, "Maximizing Gene Expression On a Plasmid Using Recombination In Vitro," *Methods in Enzymology* 68:473-82 (1979), which is hereby incorporated by reference in its entirety.

A nucleic acid molecule encoding a therapeutic protein or peptide, a promoter molecule of choice, including, without limitation, enhancers, and leader sequences, a suitable 3' regulatory region to allow transcription in the host cell, and any additional desired components, such as reporter or marker genes, are cloned into the vector of choice using standard cloning procedures in the art, such as described in Joseph Sambrook et al., MOLECULAR CLONING: A LABORATORY MANUAL (Cold Springs Harbor 1989); Frederick M. Ausubel, SHORT PROTOCOLS IN MOLECULAR BIOLOGY (Wiley 1999), and U.S. Pat. No. 4,237,224 to Cohen and Boyer, which are hereby incorporated by reference in their entirety.

Once the nucleic acid molecule encoding the peptide has been cloned into an expression vector, it is ready to be incorporated into a host cell, in this case a preparation of cortical or striatal immature interneuron precursor cells. Recombinant molecules can be introduced into the immature interneuron precursor cells and, subsequently implanted into a subject's brain for delivery of the therapeutic agent using any of the methods described supra.

EXAMPLES

The following examples illustrate various methods for compositions in the treatment method of the invention. The examples are intended to illustrate, but in no way limit, the scope of the invention.

Materials and Methods for Examples 1-6

Generation of the mES-Lhx6::GFP Line.

The previously generated Lhx6-GFP bacterial artificial chromosome (BAC) from GENSAT (Gong et al., "A Gene Expression Atlas of the Central Nervous System Based on Bacterial Artificial Chromosomes," *Nature* 425(6961):917 (2003), which is hereby incorporated by reference in its entirety) was modified for G418 selection as described previously (Tomishima et al., "Production of Green Fluorescent Protein Transgenic Embryonic Stem Cells Using the GENSAT Bacterial Artificial Chromosome Library," *Stem Cells* 25(1):39 (2007), which is hereby incorporated by reference in its entirety). This BAC, which does not express an Lhx6 transcript, was then electroporated into a mouse ES line (J1, ATCC) to generate the Lhx6::GFP line. Karyotype and FISH analysis revealed a normal chromosomal arrangement and a single BAC integration site on chromosome 13.

Cell Culture Embryonic Stem (ES) Cells.

Lhx6::GFP mouse ES cells were grown on mouse embryonic fibroblasts in ES medium [knockout DMEM (Gibco), 15% FBS (Gibco-Hyclone), L-glutamine, pen/strep, MEM nonessential amino acids, b-mercaptoethanol, and LIF (R&D)]. Prior to differentiation, ES cell colonies were passaged onto gelatin.

ES Cell Differentiation.

ES cells were treated with 0.05% trypsin and plated as single cells at 70,000 cells/mL as described (Watanabe et al., "Directed Differentiation of Telencephalic Precursors From Embryonic Stem Cells," *Nat. Neurosci.* 8(3):288 (2005), which is hereby incorporated by reference in its entirety). To enhance survival in the single cell suspension, 10 uM of the ROCK inhibitor Y27632 was added to the differentiation medium (Watanabe et al., "A ROCK Inhibitor Permits Survival of Dissociated Human Embryonic Stem Cells," *Nat Biotechnol* 25(6):681 (2007), which is hereby incorporated by reference in its entirety). Cells that became floating embryoid bodies were grown in a 1:1 mixture of KSR and N2 media for 5 days, supplemented with either noggin (250 ng/mL, R&D Systems) IGF1 (20 ng/mL), or DKK1 (100 ng/mL) (the neutralization stage). Medium was changed at differentiation day (dd) dd3, dd5, dd8, and dd11, and cultures were typically fixed and analyzed by immunofluorescence, or subjected to FACS on day 12. On dd5, embryoid bodies (EBs) were mechanically dissociated using Accutase and plated onto adherent polyornithine-laminin plates in N2 medium supplemented with bFGF (20 ng/mL, day 5-8), IGF1 (20 ng/mL, day 5-8), and SHH (200 ng/mL, d6-d12; R&D Systems). Treatment with IGF1 (20 ng/mL) from days 5-8 of differentiation further enhanced the yield of GFP+ cells independent of the treatment given during the neuralization stage. Overexpression of IGF1 is known to induce an expansion of anterior at the expense of posterior neuroectoderm during *xenopus* development (Richard-Parpaillon et al., "The IGF Pathway Regulates Head Formation by Inhibiting Wnt Signaling in *Xenopus*," *Dev Biol* 244(2):407 (2002), which is hereby incorporated by reference in its entirety) and may synergize with SHH signaling in regulating the proliferation and survival of neuronal progenitors (Rao et al., "Sonic Hedgehog and Insulin-Like Growth Factor Signaling Synergize to Induce Medulloblastoma Formation From Nestin-Expressing Neural Progenitors in Mice," *Oncogene* 23(36):6156 (2004), which is hereby incorporated by reference in its entirety). Negligible numbers of Lhx6::GFP+ cells were generated when neither noggin/DKK1 nor IGF1 were included, or when SHH was omitted from the differentiation.

Fluorescence Activated Cell Sorting (FACS).

At differentiation day 12 (dd12), cell cultures were treated with 0.05% trypsin for 5 minutes, followed by gentle titration to dissociate to single cells. The trypsin was neutralized using N2 medium with 20% FBS. The dissociated cells are then centrifuged at 1000 rpm for 5 minutes and cells resuspended in N2+20% FBS, and passed through a 40 um filter. The cell suspension was kept on ice until FACS Vantage sorting (BD Biosciences) and analyzed using FACSDiva software (BD Biosciences). Dead cells were excluded by selecting for the DAPI negative population.

Cortical Transplantation.

Cortical transplantation was conducted as described previously (Wonders et al., "A Spatial Bias for the Origins of Interneuron Subgroups Within the Medial Ganglionic Eminence," *Dev Biol* 314(1):127 (2008), which is hereby incorporated by reference in its entirety). One to two-day-old neonatal mice were cold-anesthetized until pedal reflex was abolished. After sorting for Lhx6::GFPexpressing cells by FACS, a concentrated cell suspension (~10,000 cells/µL) in neurobasal/B27 medium (Gibco) was loaded into glass pipettes and attached to a Drummond microinjector apparatus. Twenty thousand to forty thousand cells were injected into the cortical plate at the following coordinates from bregma: 2.0 mm anterior, 2.5 mm lateral, 1.0 mm dorsal, targeting cortical layers 5 and 6. Grafted pups were warmed on a heating pad and returned to their mothers.

Immunohistochemistry.

Cells were fixed in 4% paraformaldehyde and stained with the following primary antibodies: rabbit anti-LHX6 (provided by Vassilis Pachnis), FoxG1 (provided by Eseng Lai), GABA (Sigma-Aldrich), GFP (Invitrogen), Dlx2, Kv3.1 (provided by Bernardo Rudy), Tbr1 (provided by Robert Hevner), NPY (Immunostar), calretinin, mouse anti-Nkx2.1 (Neomarkers), GAD67 (Chemicon), Parvalbumin; rat anti-somatostatin (Chemicon); chicken anti-GFP (Abcam). Fluorescent secondary antibodies were from the Alexa Fluorophores (Invitrogen) and Cy5 (Jackson Immunoresearch).

Quantification of Transplant Distribution.

To identify the approximate, relative distribution of transplanted cells, brains were sectioned in the coronal plane at 50 µm on a vibrating microtome (Leica). Every fifth section was labeled with rabbit-anti GFP immunofluorescence and the nuclear stain DAPI. Profile counts of GFP+ cells in the cortex, essentially all of which had neuronal morphologies by 7 DPT, were conducted. As no cell core remained at the injection site at 7 or at 30 DPT, the section with the highest number of cell profiles was taken as the presumptive injection region and distributions were calculated in 250 µm bins extending in the rostral-caudal axis from this region. The number of cell profiles per bin was estimated by multiplying the number of profiles in the given section by 5. Since this section was located at the distal end of each bin, relative to the apparent injection region, the extrapolated counts per bin would be expected to underestimate total cell numbers (since there is a clear decline in cells with distance from the injected region). However, because profile counts were used, which can provide an overestimation of cells per section since some cells will be represented in two sections, the underestimation may not be substantial. At any rate, this method provides an efficient way to quantify relative distributions of cells across transplanted brains.

Electrophysiological Recording.

Electrophysiology was performed on mice at post-natal days 16-29 (P16-P29) that had successfully undergone transplantation as above. Animals were anesthetized and decapitated. The brain was then quickly removed and transferred to ice-cold sucrose cutting solution containing: 214 mM Sucrose, 2.5 mM KCl, 24 mM $NaHCO_3$, 1.25 mM $NaH_2PO_4$, 11 mM D-Glucose, 10 mM $MgCl_2$, and 0.5 mM $CaCl_2$ (Osmolarity ~315 mOsm) and bubbled with 5% $CO_2$/95% $O_2$. Coronal cortical slices (200-300 μm) were prepared using a vibratome (VT1000S; Leica Microsystems). Slices recovered in artificial cerebrospinal fluid (ACSF) containing: 119 mM NaCl, 2.5 mM KCl, 26.2 mM $NaHCO_3$, 2.5 mM $CaCl_2$, 1.3 mM $MgCl_2$, 1 mM $NaH_2PO_4$, and 20 mM Glucose (pH 7.4, Osmolarity ~300 mOsm) and bubbled with 5% $CO_2$/95% $O_2$ at room temperature for a minimum of one hour prior to recording. Slices were constantly perfused with ACSF during recordings.

Whole-cell recordings were made from GFP-positive neurons located in layers II-V of the cortex. GFP-positive cells were typically 40-70 μm below the surface of the slice. Patch electrodes (5-8 mOhms) were filled with intracellular solution containing: 130 mM K-Gluconate, 16 mM KCl, 2 mM $MgCl_2$, 10 mM HEPES, 0.2 mM EGTA, 4 mM Na2-ATP, and 0.4 mM Na3-GTP (pH 7.25 Osmolarity ~290 mOsm). For post-recording immunocytochemistry, 0.5% Biocytin Alexa Fluor 546 was included in the internal solution.

All recordings were performed in current-clamp mode (Axopatch 200B; Axon Instruments) and analyzed offline in Igor version 4.0 and Excel. Standard electrophysiological protocols were followed throughout. The membrane potential of each cell was identified shortly after rupturing the patch and periodically during the course of the experiment to ensure there was no significant deterioration of the health of the cell. Spontaneous miniature synaptic currents were recorded in the presence of TTX in voltage-clamp mode at −60 mV. Depolarizing and hyperpolarizing current steps (0.2 Hz; duration 500 ms) were applied to the cells to help characterize their electrophysiological profile. Cells that showed significant rundown were discarded. All parameters were measured for a minimum of three trials for each cell, and the average value was calculated. Spike threshold for each cell was identified with incremental 5 pA steps until action potentials were triggered. Firing characteristics of individual cells were measured between threshold and maximal firing frequency until failure. To test whether injection of hyperpolarizing current resulted in rebound spike activity, neurons were stepped between −40 and −100 mV.

Cells were classified according to the criteria established by Fishell and colleagues (Butt et al., "The Temporal and Spatial Origins of Cortical Interneurons Predict Their Physiological Subtype," Neuron 48(4):591 (2005), which is hereby incorporated by reference in its entirety) and the Petilla conference (Ascoli et al., "Petilla Terminology: Nomenclature of Features of GABAergic Interneurons of the Cerebral Cortex," Nat Rev Neurosci 9(7):557 (2008), which is hereby incorporated by reference in its entirety). Briefly, cells that fire at >50 Hz, exhibit a consistent inter-spike interval with little to no adaptation, exhibit a deep, fast afterhyperpolarization (AHP), and exhibit no rebound spike activity are categorized as fast spiking (FS). Cells that were non-FS (NFS) were categorized into three groups: stuttering, adapting or accommodating (NFS1), or nonadapting (NFS2). Both NFS1 and NFS2 cells have small biphasic AHPs and a pronounced delay to spike at threshold, but most of the NFS1 cells exhibit considerable adaptation in spike frequency, whereas NFS2 cells often do not (Miyoshi et al., 2007).

For postrecording immunocytochemistry, 0.5% Neurobiotin (Vector Labs) was included in the internal solution. After recording, slices were fixed in 4% PFA for 4 h and proceeded to perform immunohistochemical analysis for GFP (Abcam chicken anti-GFP, Alexa goat anti-chicken 488), Neurobiotin (Jackson ImmunoResearch streptavidin-conjugated 546), and either PV (mouse anti-PV, Millipore Bioscience Research Reagents; donkey anti-mouse Cy5, Jackson ImmunoResearch) for fast-spiking cells (7 of 19 recorded) or somatostatin (rat anti-Sst, Millipore Bioscience Research Reagents; donkey anti-rat Cy5, Jackson ImmunoResearch) for the non-FS cells (12 of 19).

Example 1

Generation of Mouse Embryonic Stem Cell-Derived Interneuronal Precursors

Figures 1A, 1B, 1C, 1D, 1E, 1F, 1G, 1H:
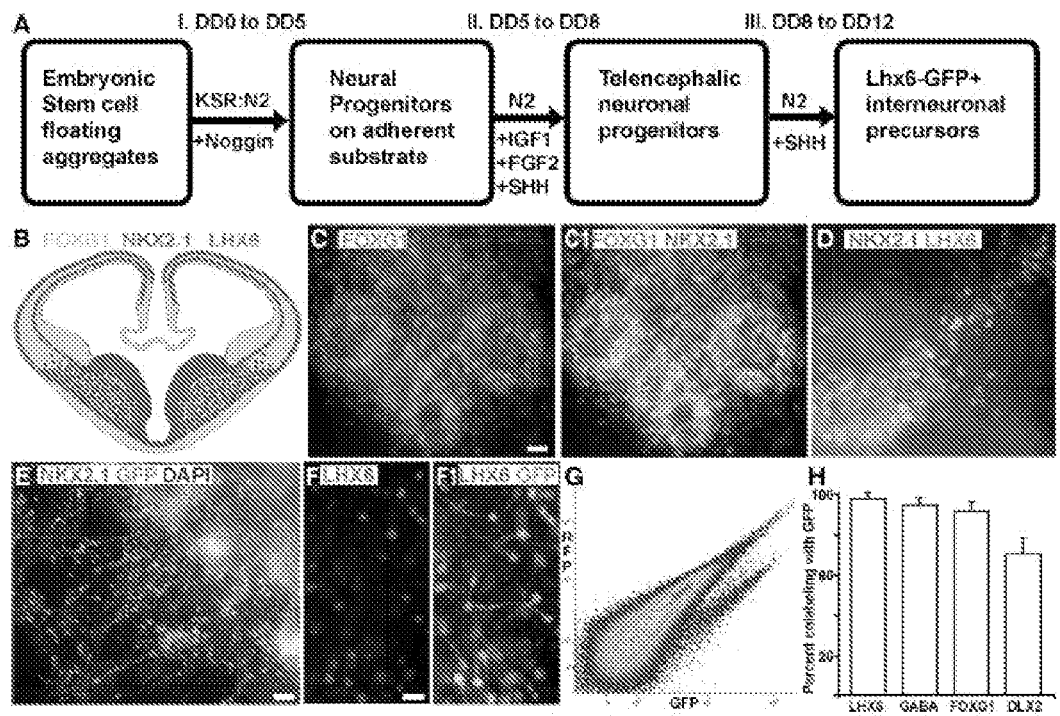
FIGS. 1A-1H depict the generation of mouse embryonic stem cell (mESC) derived interneuronal precursors. The paradigm for differentiating ES cells toward ventral forebrain progenitors is shown in FIG. 1A.

Previous work has demonstrated that ESCs can be directed toward telencephalic progenitors, including those that differentiate into neurons expressing the generally inhibitory neurotransmitter GABA (Watanabe et al., "Directed Differentiation of Telencephalic Precursors From Embryonic Stem Cells," Nat Neurosci 8(3):288 (2005) and Gaspard et al., "An Intrinsic Mechanism of Corticogenesis From Embryonic Stem Cells," Nature 455(7211):351 (2008), which are hereby incorporated by reference in their entirety). Since FoxG1+ and Nkx2.1+ progenitors give rise both to GABAergic interneurons and projection neurons (Fogarty et al., "Spatial Genetic Patterning of the Embryonic Neuroepithelium Generates GABAergic Interneuron Diversity in the Adult Cortex," J Neurosci 27(41):10935 (2007) and Xu et al., "Fate Mapping Nkx2.1-Lineage Cells in the Mouse Telencephalon," J Comp Neurol 506(1):16 (2008), which are hereby incorporated by reference in their entirety), whether cortical or striatal GABAergic interneurons could be generated from mouse ES cells was determined. Using a modified protocol for the generation of ventral telencephalic cells (FIGS. 1A and 1B), it was found that mES cells can be directed to differentiate and aggregate into rosette-like clusters that strongly express both FoxG1 and Nkx2.1 (FIGS. 1C and 1C1). By dd12, streams of cells appeared to emanate from these Nkx2.1+ clusters, and they expressed Lhx6 (FIG. 1D), a marker of most MGE-derived interneurons that is expressed from shortly before cell cycle exit through post-natal maturation (Lavdas et al., "The Medial Ganglionic Eminence Gives Rise to a Population of Early Neurons in the Developing Cerebral Cortex," Journal of Neuroscience 19(18):7881 (1999); Liodis et al., "Lhx6 Activity is Required for the Normal Migration and Specification of Cortical Interneuron Subtypes," J Neurosci 27(12):3078 (2007); and Du et al., "NKX2.1 Specifies Cortical Interneuron Fate by Activating Lhx6," Development 135:1559-1567 (2008), which are hereby incorporated by reference in their entirety).

Using an established protocol (Tomishima et al., "Production of Green Fluorescent Protein Transgenic Embryonic Stem Cells Using the GENSAT Bacterial Artificial Chromosome Library," Stem Cells 25(1):39 (2007), which is hereby incorporated by reference in its entirety) ESC lines containing an Lhx6-GFP bacterial artificial chromosome were generated that produce accurate reporter expression in Lhx6-expressing cells in vivo (Gong et al., "A Gene Expression Atlas of the Central Nervous System Based on Bacterial Artificial Chromosomes," *Nature* 425(6961):917 (2003), which is hereby incorporated by reference in its entirety). Several GFP-expressing lines were generated and confirmed to express LHX6 protein (FIG. 1F) and GFP (FIG. 1F1), and one of these lines, confirmed to have a normal karyotype, was chosen for detailed characterization. While the high-density droplet method of plating the embryoid bodies on day 5 consistently produced GFP+ cells, GFP+ cells were also observed in the "en bloc" method described by Watanabe et al., "Directed Differentiation of Telencephalic Precursors From Embryonic Stem Cells," *Nat Neurosci* 8(3):288 (2005), which is hereby incorporated by reference in its entirety, and when the cells were plated in a high-density dissociated monolayer (FIGS. 7D-7L2). No FoxG1, Nkx2.1, or GFP expression was detected at day 12 when embryoid bodies were plated as single cells at clonal density, precluding analysis of whether rosette-like clusters of Nkx2.1+ and FoxG1+ cells derive from single progenitors. Although all three successful plating protocols produced Lhx6-GFP+ cells that colabel with GABA, most GABA-expressing cells in these cultures did not express Lhx6-GFP (FIGS. 7G-7I). Since nearly all of the cells showing immunofluorescent signal for LHX6 were also GFP-expressing (FIG. 1F1), this result is consistent with the notion that this protocol, like the forebrain itself, generates a diverse group of neuronal precursors.

Lhx6-GFP+ cells were isolated by FACS, and the GFP+ cells, which were ~2% of the total viable cells (FIG. 1G), were characterized after acute plating. These cells expressed the general telencephalic marker FoxG1 (91.6±4.4%), the subpallial marker Dlx2 (70.5±7.7%), Lhx6 itself (97.7±3.1%), and GABA (94.6±3.7%) (FIG. 1H). Very rarely (<1%) did Lhx6-GFP+ cells express the pallial progenitor marker Pax6 or Tbr1, a marker of most postmitotic neurons derived from the cerebral cortical proliferative zone.

Figures 2A, 2B, 2C, 2D, 2E, 2F, 2G, 2H:
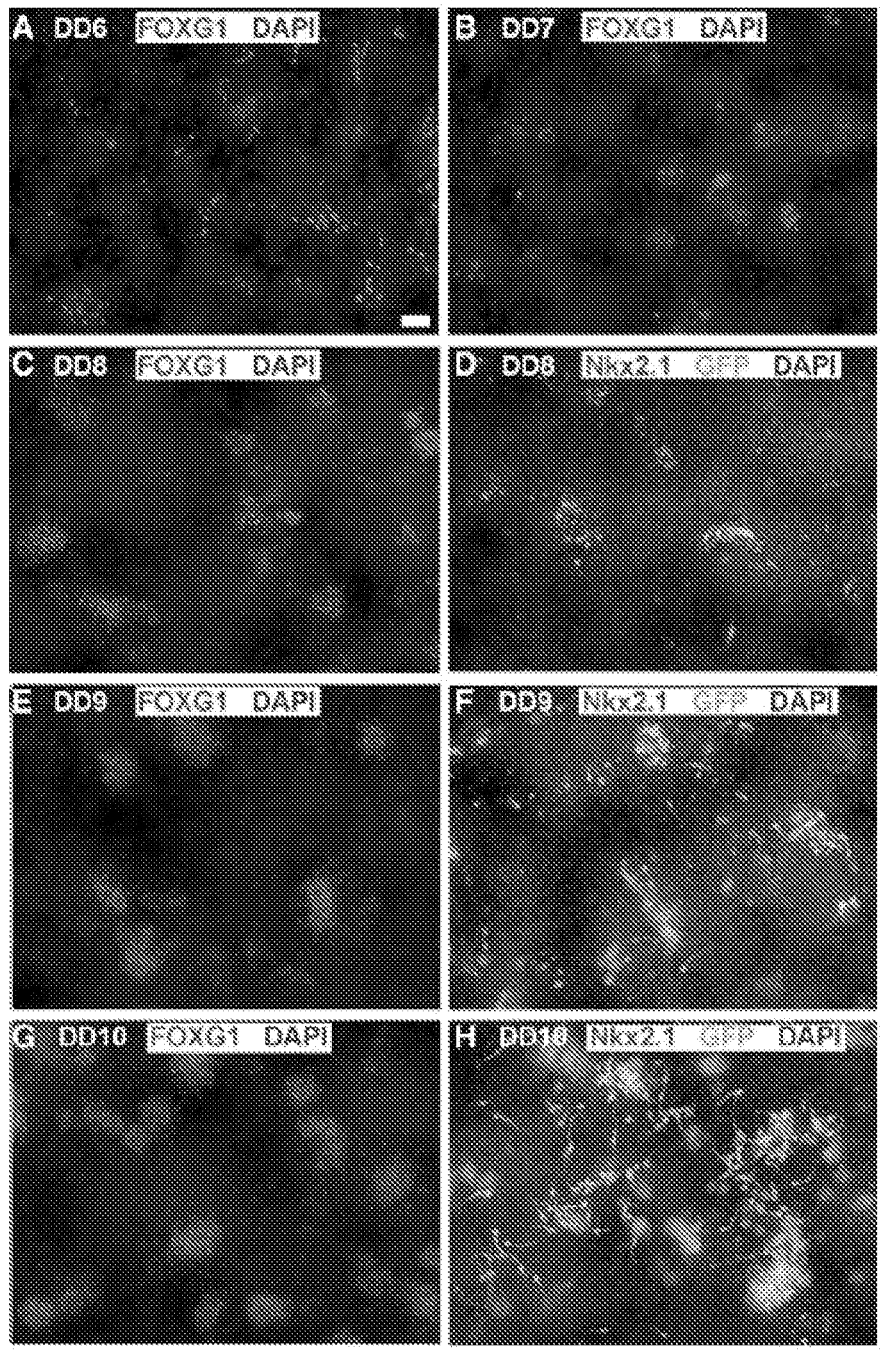
FIGS. 2A-2H show the development of FoxG1, Nkx2.1, and GFP expression in mouse ES Lhx6-GFP-derived cultures. Cells were differentiated by the protocol described in FIG. 1A, in which floating embryoid bodies are dissociated and plated on adherent substrate at dd5. Blue signal shows the nuclear staining for DAPI in all panels. The telencephalic marker FoxG1 begins to be expressed in scattered cells by 1 d after plating (dd6) (FIG. 2A), and clusters of these cells increase in size and number through dd10 (FIGS. 2B, 2C, 2E, and 2G). Nkx2.1 (red signal), expressed in a substantial subset of FoxG1+ cells in these cultures (FIG. 1C1), is expressed in a few scattered cells at day 7 (FIG. 2D) and increases similarly to FoxG1 expression through day 10 (FIGS. 2F and 2H). Lhx6-GFP expression (green signal) is apparent in differentiating-appearing, process-bearing cells that often occur adjacent to Nkx2.1+ clusters. Lhx6-GFP expression is rare at dd8 (FIG. 2D), and increases substantially by dd10 (FIG. 2H). Scale bar, 100 μm.

Using the protocol described in FIG. 1A, the temporal expression of ventral transcription factors FoxG1, Nkx2.1, and Lhx6-GFP was determined. After dissociating the embryoid bodies and plating the cells onto an attachable substrate in high-density droplets, a few FoxG1+ cells appeared scattered throughout the culture on 1 day after plating (dd6) (FIG. 2A). By ddb rosette-like clusters began to form (FIGS. 2C-2D). Nkx2.1+ cells, expressed by a subset of those that express FoxG1 (FIG. 1C1), are delayed relative to FoxG1 by ~1 day but follow a similar pattern through dd10 (FIGS. 2D, 2F, and 2H). GFP is apparent in a few cells at dd7, and also expands considerably through dd10 (FIGS. 2D, 2F, and 2H). This progression of FoxG1, Nkx2.1, and Lhx6 expression parallels events occurring in the ventral telencephalon from embryonic day 9 to embryonic day 12.

Example 2

Transplantation, Migration and Survival of Lhx6::GFP Cells

To characterize the fate potential of the Lhx6::GFP line, cells were differentiated for 11 days (FIG. 1A), collected by FACS for GFP expression (FIG. 1G), and transplanted into neonatal mouse cortex. Medial ganglionic eminence (MGE)-derived progenitors transplanted into both neonatal and adult mouse cortex have been shown to migrate, survive, and differentiate into several subgroups of cortical interneurons (Wichterle et al., "Young Neurons From Medial Ganglionic Eminence Disperse in Adult and Embryonic Brain," *Nature Neuroscience* 2(5):461 (1999); Cobos et al., "Mice Lacking Dlx1 Show Subtype-Specific Loss of Interneurons, Reduced Inhibition and Epilepsy," *Nat Neurosci* 8(8):1059 (2005); Wonders et al., "A Spatial Bias for the Origins of Interneuron Subgroups Within the Medial Ganglionic Eminence," *Dev Biol* 314(1):127 (2008); Alvarez-Dolado et al., "Cortical Inhibition Modified by Embryonic Neural Precursors Grafted into the Postnatal Brain," *J Neurosci* 26(28):7380 (2006); and Fogarty et al., "Spatial Genetic Patterning of the Embryonic Neuroepithelium Generates GABAergic Interneuron Diversity in the Adult Cortex," *J Neurosci* 27(41):10935 (2007), which are hereby incorporated by reference in their entirety). Relative to progenitors of the cortex or the lateral ganglionic eminence (LGE), this migration was found to be unique to MGE-derived progenitors (Wichterle et al., "Young Neurons From Medial Ganglionic Eminence Disperse in Adult and Embryonic Brain," *Nature Neuroscience* 2(5):461 (1999), which is hereby incorporated by reference in its entirety).

Figures 3A, 3B, 3C, 3D, 3E:
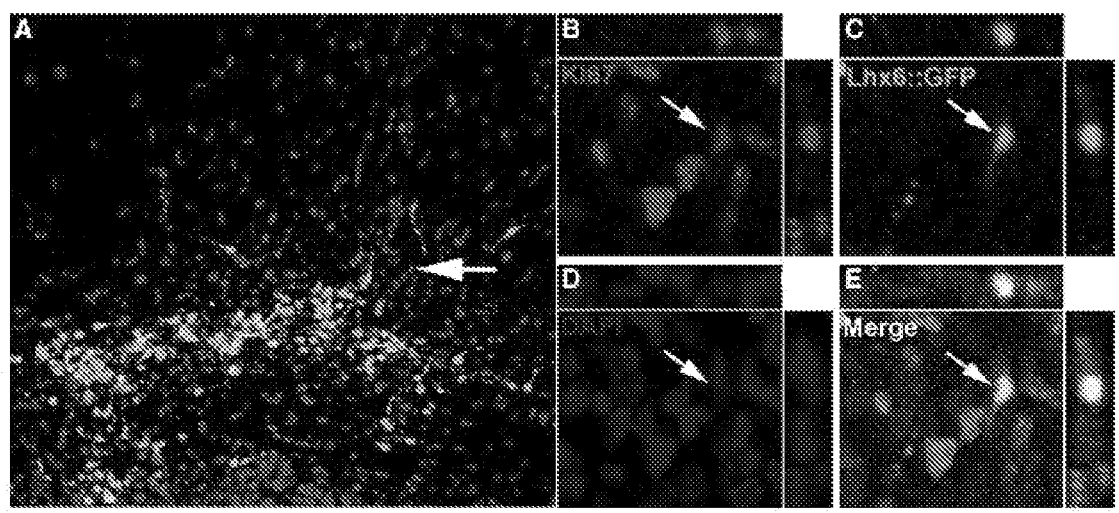
FIGS. 3A-3E show that nearly all Lhx6::GFP+ cells are post-mitotic 1 day of transplantation.
Figures 4A, 4B, 4C, 4D, 4E, 4F, 4G, 4H, 4I:
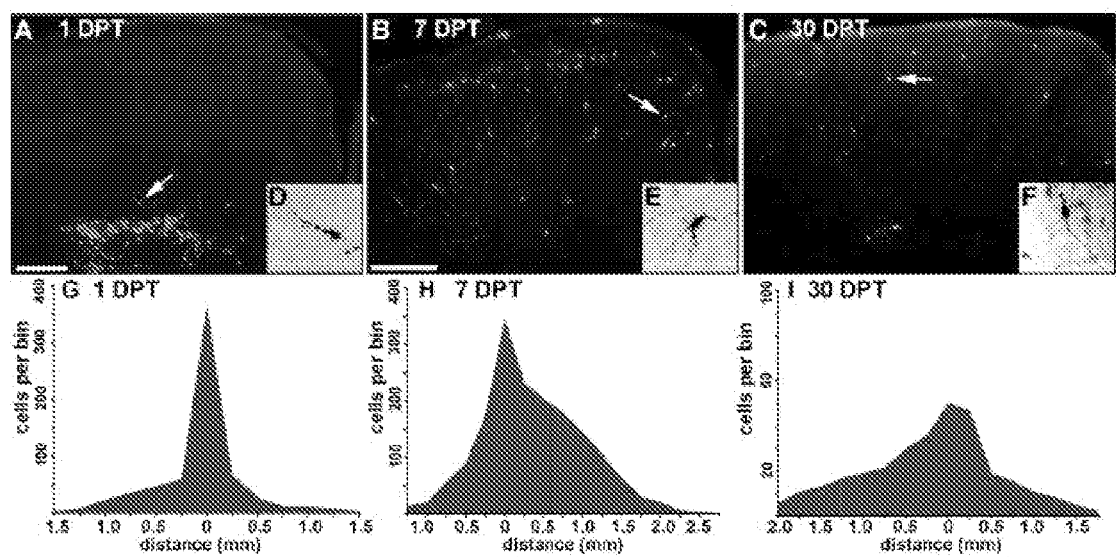
FIGS. 4A-4I depict the migration and survival of Lhx6::GFP+ cells transplanted into neonatal cortex.

One day after transplantation into layers 5-6 of the cortex, Lhx6::GFP+ cells were distributed close to the injection site, with many cells exhibiting a bipolar morphology typical of migrating interneurons (FIGS. 3A and 4A). Consistent with previous findings that Lhx6 begins to be expressed around the time of cell cycle exit (Du et al., "NKX2.1 Specifies Cortical Interneuron Fate by Activating Lhx6," *Development* 135(8):1559 (2008) and Lavdas et al., "The Medial Ganglionic Eminence Gives Rise to a Population of Early Neurons in the Developing Cerebral Cortex," *Journal of Neuroscience* 19(18):7881 (1999), which are hereby incorporated by reference in their entirety), there was minimal co-labeling of GFP and Ki-67 at 1 day post transplant (DPT) (compare FIGS. 3B and 3C). Indeed, no tumors were found in any of the transplants analyzed at any age.

Figures 5A, 5B, 5C, 5D, 5E:
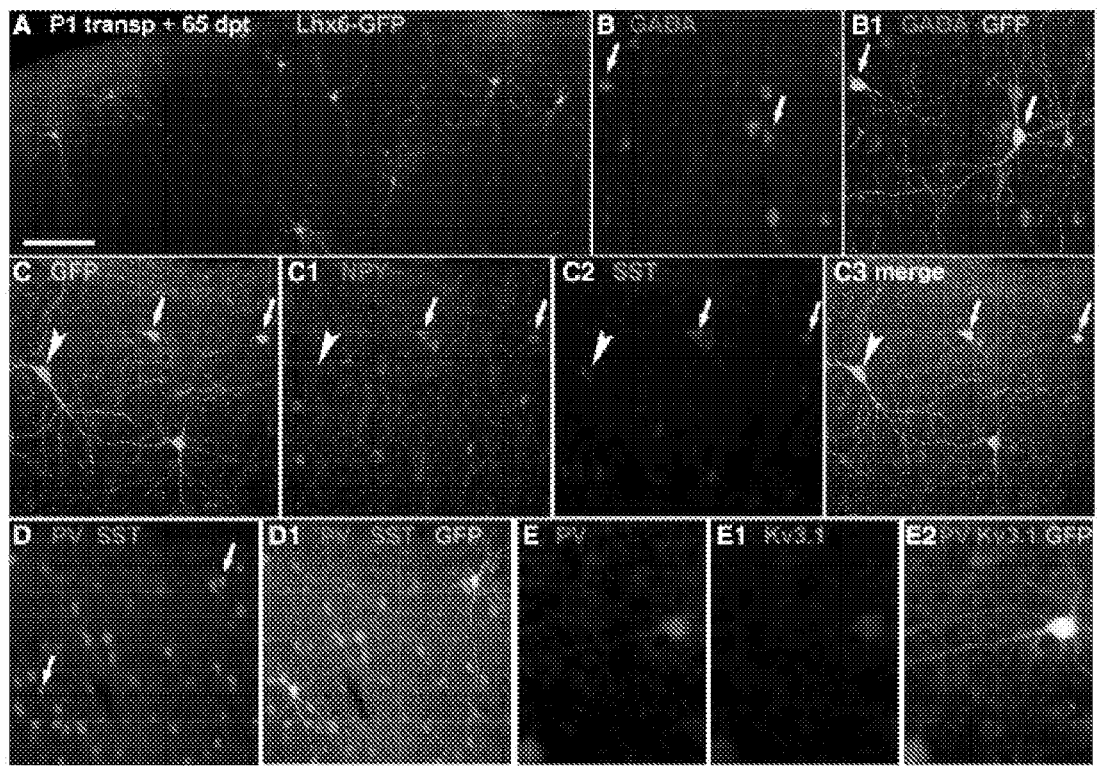
FIGS. 5A-5E show that the transplantation of mES derived Lhx6::GFP+ cells into postnatal cortex gives rise to interneuron-like cells. Lhx6::GFP cells were differentiated, collected by FACS, then transplanted into the cortical plate of neonatal pups. Shown is immunolabeling of 50 μm coronal sections taken 65 days post transplant (DPT).

By 7 DPT GFP+ cells were distributed throughout cortical layers 2-6 and dispersed over a 2 mm wide range along both the rostral-caudal and the medial-lateral axes, with some cells reaching a distance of 3 mm from the injection site (FIG. 4B). Many of the GFP+ cells at 7 DPT assumed multipolar morphologies typical of differentiating, post-migratory interneurons (FIG. 4E). At 30 DPT (FIG. 4C), cells exhibiting more complex neuritic arbors (FIG. 3F) were distributed over a similar range as at 7 DPT, but smaller total numbers of GFP+ cells were observed. Quantification of the distribution of GFP+ cells along the rostral-caudal axis from the injection site at 1, 7, and 30 DPT is presented in FIGS. 4G-4I, respectively. These data suggest that migration is completed within one week after transplantation. The decrease in the number of GFP+ cells at 30 DPT (1% of grafted cells vs. 10% of grafted cells at 7 DPT) may be due to cell death in vivo or loss of GFP expression between 7 DPT and 30 DPT. However, the surviving GFP+ population at 30 DPT appears relatively stable, as similar cell numbers and distribution is observed at 65 DPT (FIG. 5A). Transplanted GFP+ neurons remain detectable for at least 240 DPT (FIGS. 8A-8B).

Example 3

Cortical Interneuron-Like Differentiation of Lhx6::GFP Cells

Extensive migration after transplantation into neonatal cortex is highly similar to that previously reported for MGE-derived interneuron progenitors (Wonders et al., "A Spatial Bias for the Origins of Interneuron Subgroups Within the Medial Ganglionic Eminence," *Dev Biol* 314(1):127 (2008) and Alvarez-Dolado et al., "Cortical Inhibition Modified by Embryonic Neural Precursors Grafted into the Postnatal Brain," *J Neurosci* 26(28):7380 (2006), which are hereby incorporated by reference in their entirety). To determine whether ESC-derived cells acquire neurochemical characteristics of cortical interneurons, transplanted Lhx6::GFP cells were examined by immunofluorescence for interneuron markers at 30 and 65 DPT (FIG. 5). Like MGE-derived cortical interneurons, most GFP+ cells expressed GABA (FIGS. 5B and 5B1; n=5; 161/189; 85.7%+/−3.5%), as well as the subgroup-specific markers parvalbumin (PV) or somatostatin (Sst) (FIGS. 5C3 and 5D1). Typical of "native" PV+ interneurons, most GFP+ neurons that colabeled for PV also expressed the potassium channel Kv3.1 (38/39 cells) (FIGS. 5E-5E2). Typical of native Sst-expressing interneurons, GFP+ neurons that colabeled for Sst did not express PV or Kv3.1, but did frequently co-label with neuropeptide Y (NPY) (present in 57 of 179 cells colabeled for Sst and GFP+ cells) (FIGS. 5C-5C3). Counts of cells in triple labeled (PV-Sst-GFP) sections from 4 mice transplanted with independently-cultured cells revealed that out of 290 GFP+ cells, 185 (64%) co-expressed Sst, and 30 (10%) express PV. Labeling of Lhx6-GFP+ neurons for calretinin was infrequent, and was accompanied by co-labeling with Sst. The strong bias for Sst over PV expressing interneurons is similar to that found following neonatal transplantation of dorsal MGE progenitors (Flames et al., "Delineation of Multiple Subpallial Progenitor Domains by the Combinatorial Expression of Transcriptional Codes," *J Neurosci* 27(36):9682 (2007) and Wonders et al., "A Spatial Bias for the Origins of Interneuron Subgroups Within the Medial Ganglionic Eminence," *Dev Biol* 314(1):127 (2008), which are hereby incorporated by reference in their entirety). In sum, Lhx6::GFP ES cells can be differentiated into neurons that express appropriate combinations of proteins known to be present in Lhx6+ interneuron subpopulations in the mouse cerebral cortex.

Example 4

Transplanted Lhx6::GFP+ Cells have MGE-Interneuron-Like Spiking Characteristics

The data on cell migration and neurochemical differentiation strongly suggest that Lhx6::GFP+ cells differentiate into functional neurons that exhibit features of MGE-derived cortical interneuron subgroups in vivo. To test this directly, electrophysiological studies were performed to examine the biophysical properties and the functional incorporation of transplanted Lhx6::GFP+ cells in situ. Under the visual guidance of fluorescence illumination, whole-cell patch-clamp recordings were performed on GFP+ cells in acutely prepared cortical slices between 14 and 26 DPT (FIGS. 6A-6K). A total of 45 GFP+ cells were recorded (see Table 1) with an average resting membrane potential (RMP) of −54.7±6.5 mV.

TABLE 1

Electrophysiological Characteristics of Lhx6::GFP+ Cells After Transplantation into Neonatal Cortex, Based on Whole-Cell Patch-Clamp Recordings

| Age | Interneuron type | No. cells | Avg. RMP (mV; ±SD) |
| --- | --- | --- | --- |
| 14 | Immature | 3 | −44 ± 6 |
| 20-26 | Immature | 7 | −44 ± 4.4 |
| 20-26 | NFS2 | 11 | −57.2 ± 6.8 |
| 20-26 | NFS1 | 7 | −59.2 ± 9.9 |
| 20-26 | C-STUT | 6 | −60.2 ± 6.3 |
| 20-26 | FS | 11 | −63.5 ± 6 |

Figures 6A, 6B, 6C, 6D, 6E, 6F, 6G, 6H, 6I, 6J, 6K:
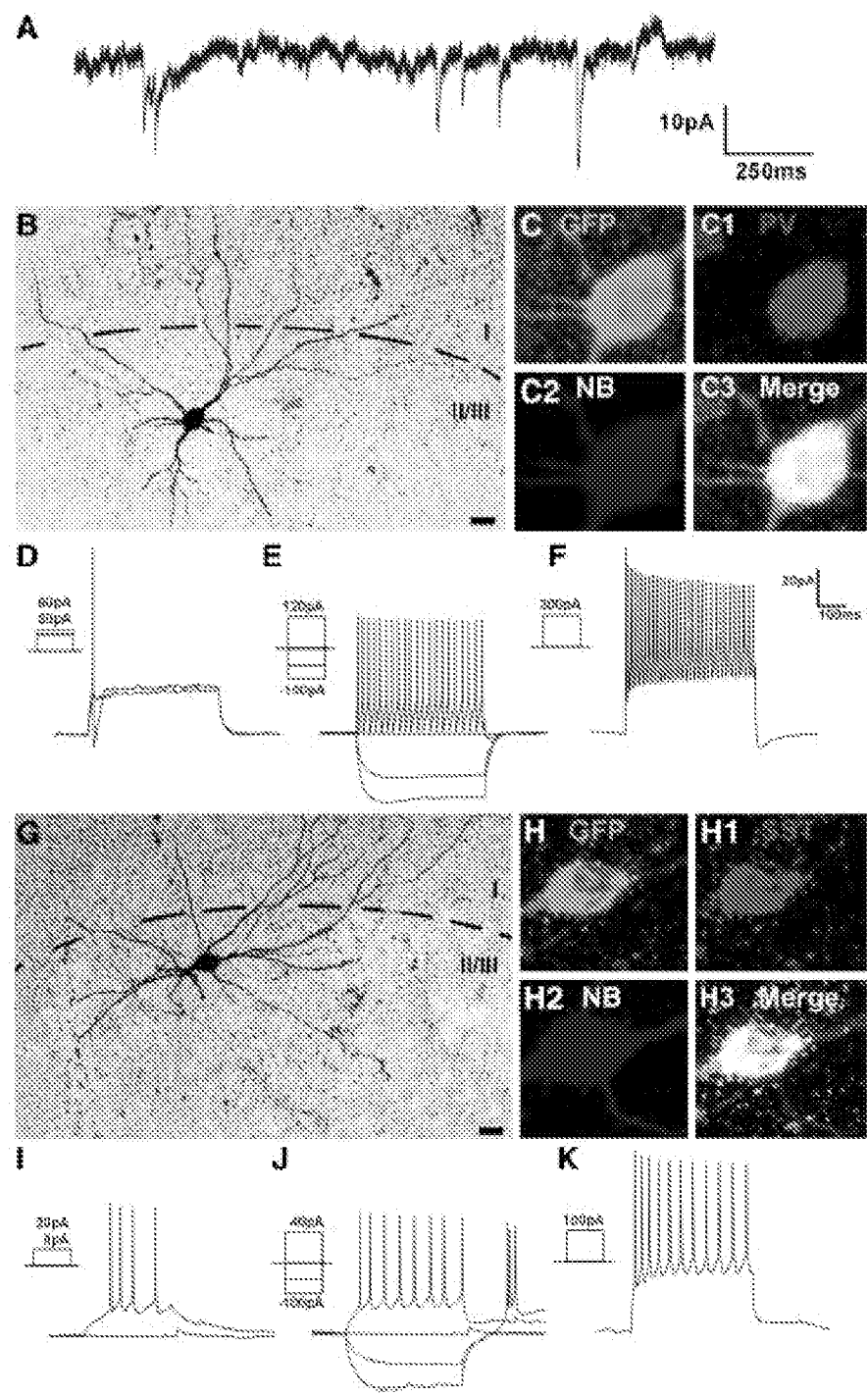

As expected, some cells recorded at early time points exhibited immature firing characteristics (n=10, including all 3 cells from 14 DPT and 7 cells between 20 and 26 DPT), such as a less hyperpolarized resting membrane potential (average RMP=−43.6±5.2 mV) and a higher threshold for firing action potentials. In contrast, cells recorded at later time points exhibited more hyperpolarized resting membrane potentials (average RMP=−60±7.2 mV) and firing properties characteristic of cortical interneurons (FIGS. 6D-6F, 6I-6K, and Table 1). These included FS and three classes of NFS patterns, stuttering nonpyramidal, NFS1 (accommodating), and NFS2 (nonaccommodating) (Kawaguchi et al., "Physiological and Morphological Identification of Somatostatin- or Vasoactive Intestinal Polypeptide-Containing Cells Among GABAergic Cell Subtypes in Rat Frontal Cortex," *J. Neurosci.* 16(8):2701 (1996); Markram et al., "Interneurons of the Neocortical Inhibitory System," *Nat. Rev. Neurosci.* 5(10):793 (2004); Butt et al., "The Temporal and Spatial Origins of Cortical Interneurons Predict Their Physiological Subtype," *Neuron* 48(4):591 (2005), which are hereby incorporated by reference in their entirety). NFS patterns frequently correlate with Sst expression, while cells exhibiting fast-spiking firing patterns are typical of the PV-expressing interneuron subgroup (Kawaguchi et al., "Physiological and Morphological Identification of Somatostatin- or Vasoactive Intestinal Polypeptide-Containing Cells Among GABAergic Cell Subtypes in Rat Frontal Cortex," *J. Neurosci.* 16(8):2701 (1996), which is hereby incorporated by reference in its entirety). Three of seven fast-spiking neurons (maximal firing rate >50 Hz at room temperature) expressed detectable levels of PV (FIG. 6C), while 8/12 non-FS neurons expressed Sst (FIG. 6H). Finally, under voltage-clamp conditions, GFP+ cells displayed spontaneous (nonevoked) synaptic currents (FIG. 6A), suggesting that they receive synaptic inputs.

Example 5

Mouse ESC-Derived Lhx6::GFP+ Cells Differentiate into Interneurons after Transplantation into Epileptic Adult Cortex To establish the feasibility of using Lhx::GFP+ cells in a cell based therapy for seizures, a chronic seizure focus was made using microinjection of TTX in the adult mouse cortex. One month thereafter, Lhx::GFP+ cells were transplanted into the seizure focus. Two months later the cells appear to migrate, survive and differentiate (FIG. 9) in a manner highly similar to that reported using neonatal transplants and published in Maroof et al., "Prospective Isolation of Cortical Interneuron Precursors from Mouse Embryonic Stem Cells," *J. Neurosci.* 30(13):4667-75 (2010), which is hereby incorporated by reference in its entirety. Testing effects of these transplants on seizure propagation is ongoing, but the experiment demonstrates that Lhx::GFP+ cells are able to disperse and survive following transplantation into a seizure focus in adult mammalian cortex. The results presented in FIG. 9 indicated that Lhx6-GFP+ cells, either by their intrinsic ability to act as inhibitory interneurons, or as a drug delivery vehicle, have excellent potential for use in cell based therapy for seizures.

Discussion of Examples 1-5

GABAergic interneuron precursors from the MGE have the remarkable ability to migrate, differentiate, and function after transplantation into postnatal neocortex (Wichterle et al., "Young Neurons From Medial Ganglionic Eminence Disperse in Adult and Embryonic Brain," *Nature Neurosci-* ence 2(5):461 (1999); Cobos et al., "Mice Lacking Dlx1 Show Subtype-Specific Loss of Interneurons, Reduced Inhibition and Epilepsy," *Nat. Neurosci.* 8(8):1059 (2005); Alvarez-Dolado et al., "Cortical Inhibition Modified by Embryonic Neural Precursors Grafted into the Postnatal Brain," *J. Neurosci.* 26(28):7380 (2006); Fogarty et al., "Spatial Genetic Patterning of the Embryonic Neuroepithelium Generates GABAergic Interneuron Diversity in the Adult Cortex," *J. Neurosci.* 27(41):10935 (2007); Wonders et al., "A Spatial Bias for the Origins of Interneuron Subgroups Within the Medial Ganglionic Eminence," *Dev. Biol.* 314 (1):127 (2008), which are hereby incorporated by reference in their entirety). These characteristics make them attractive candidates for use in cell-based therapy, either by their intrinsic activity or as a vector for drug delivery, but such therapy would require the use of large numbers of cells. To demonstrate that MGE-like interneurons can be generated from ESCs, the transcription factor Lhx6, which is expressed from around the time these neurons exit the cell cycle, through the phases of migration and initial differentiation, and into adulthood was used to generate a mouse ES line containing the Lhx6-GFP BAC construct. Use of this construct allowed for both the FACS collection of MGE-like interneuron precursors (FIG. 1), and the identification of these cells months after transplantation into the postnatal neocortex (FIGS. 4-5).

Despite the relatively low percentage of GFP+ cells generated (~2%), FACS collection results in hundreds of thousands of GFP+ cells per experiment being generated for transplantation studies (FIG. 1G). Comparison of the results of these transplantations with similar neocortical transplantations of MGE-derived progenitors suggests that the Lhx6::GFP line can be used to generate GFP+ cells with a differentiation potential remarkably similar to MGE progenitors (FIGS. 2-6) (Cobos et al., "Mice Lacking Dlx1 Show Subtype-Specific Loss of Interneurons, Reduced Inhibition and Epilepsy," *Nat Neurosci* 8(8):1059 (2005); Alvarez-Dolado et al., "Cortical Inhibition Modified by Embryonic Neural Precursors Grafted into the Postnatal Brain," *J Neurosci* 26(28):7380 (2006); Flames et al., "Delineation of Multiple Subpallial Progenitor Domains by the Combinatorial Expression of Transcriptional Codes," *J Neurosci* 27(36):9682 (2007); Wonders et al., "A Spatial Bias for the Origins of Interneuron Subgroups Within the Medial Ganglionic Eminence," *Dev Biol* 314(1):127 (2008), which are hereby incorporated by reference in their entirety). Like MGE transplants into neonatal neocortex, Lhx6::GFP cells migrate extensively during the first week after transplantation (FIG. 4). However, detection of GFP+ cells drops from ~10% at 1 week to 2% at 1 month, whereas MGE transplant survival into neonatal cortex ranges from 10 to 20% after several weeks. There are a number of potential sources for this discrepancy. First, MGE transplants contain many Nkx2.1+ mitotic progenitors of the ventricular zone (VZ) and the subventricular zone (SVZ), whereas here transplanted cells are exclusively at the Lhx6+ stage more characteristic of a subpopulation of MGE mantle zone cells. Second, the FACS sorting itself could influence long-term survivability. Third, MGE transplant experiments have mainly involved host and donor animals of the same strain, whereas here the ES-line cells derive from the inbred 129J strain, while the host animals were of the highly outbred CD1 line, raising the possibility of substantial immune response. Finally, the possibility of silencing of the GFP reporter in many cells can not be ruled out. It has recently been reported that cholinergic striatal interneurons briefly express Lhx6 at the progenitor or immediately postmitotic stage (Fragkouli et al., "LIM Homeodomain Transcription Factor-Dependent Specification of Bipotential MGE Progenitors into Cholinergic and GABAergic Striatal Interneurons," *Development* 136:3841-3851 (2009), which is hereby incorporated by reference in its entirety). This population is quite small relative to the GABAergic interneuron subpopulations of the striatum and cortex that maintain Lhx6 expression, but could be overrepresented in the conditions produced by the protocol used. Future studies will be needed to compare these results to those from transplantations of Lhx6::GFP+ cells tagged also with a constitutively expressed marker, to Lhx6::GFP+ cells generated by alternative protocols, to transplantations of FACS sorted, MGE cells from Lhx6-GFP-expressing transgenic mice, and to transplantations into immune-suppressed and 129J strain hosts.

Regardless of the survival issue, transplantations of Lhx6::GFP cells result in the successful grafting of large numbers of cells that can be studied after their maturation in vivo. Transplanted cells tend to have general morphologies of Lhx6-expressing cortical interneurons, including multipolar dendritic arborizations and aspiny dendrites (FIG. 5 and FIGS. 6B, 6G). As occurs for Lhx6+ cells in vivo, the majority of transplanted Lhx6::GFP cells express either SST or PV (FIG. 5). Importantly, colabeling reveals that markers that are coexpressed with these subgroups, such as KV3.1 with the PV+ subgroup and NPY with some of the SST-expressing cells, are appropriately expressed in the transplanted ES-derived interneurons (FIG. 5). In addition, whole-cell patch-clamp recordings during the third and fourth postnatal weeks reveals neuronal characteristics, the presence of synaptic inputs, and spiking characteristics typical of Lhx6-expressing interneuron subgroups (FIG. 6). A recent study found that ES-derived neural precursor cells (ES-NPCs) were capable of forming distinct, subcortical projections to distant axonal targets based on where the ES-NPCs were transplanted in the cortex, suggesting that defined progenitors retain the intrinsic capacity to form connections within the CNS (Ideguchi et al., "Murine Embryonic Stem Cell Derived Pyramidal Neurons Integrate into the Cerebral Cortex and Appropriately Project Axons to Subcortical Targets," *J Neurosci* 30:894-904 (2010), which is hereby incorporated by reference in its entirety). While further studies will be needed to fully describe the multiple types of interneurons generated in these studies at the important levels of axon targeting and downstream influences on single neuron, network activity, and animal behavior, the lines of evidence presented above strongly support the notion that the Lhx6::GFP ES line can be differentiated into interneuron-like cells.

The bias for Sst+ interneurons over those that express PV was unexpected, since there are approximately two times more PV+ than Sst+ interneurons in mouse cortex (Tamamaki et al., "Green Fluorescent Protein Expression and Colocalization with Calretinin, Parvalbumin, and Somatostatin in the GAD67-GFP Knock-In Mouse," *Journal of Comparative Neurology* 467:60 (2003), which is hereby incorporated by reference in its entirety). The timing of FACS collection would not be expected to affect this ratio, as no overall differences in the birthdate of Sst+ versus PV+ subgroups are found within a given cortical layer (Wonders et al., "A Spatial Bias for the Origins of Interneuron Subgroups Within the Medial Ganglionic Eminence," *Dev Biol* 314(1):127 (2008), which is hereby incorporated by reference in its entirety). However, based both on transplantation studies and genetic fate mapping, recent evidence suggests that within the MGE there is a partial bias for the generation of PV-expressing interneuron subgroups in the more ventral region of the MGE, while Sst-expressing subgroups are preferentially produced from progenitors located in the dorsal MGE (Flames et al., "Delineation of Multiple Subpallial Progenitor Domains by the Combinatorial Expression of Transcriptional Codes," *J Neurosci* 27(36):9682 (2007); Fogarty et al., "Spatial Genetic Patterning of the Embryonic Neuroepithelium Generates GABAergic Interneuron Diversity in the Adult Cortex," *J Neurosci* 27(41):10935 (2007), Wonders et al., "A Spatial Bias for the Origins of Interneuron Subgroups Within the Medial Ganglionic Eminence," *Dev Biol* 314(1):127 (2008), and Xu et al., "Fate Mapping Nkx2.1-Lineage Cells in the Mouse Telencephalon," *J Comp Neurol* 506(1):16 (2008), which are hereby incorporated by reference in their entirety). This result suggests that the ventral telencephalic differentiation protocol used here preferentially directs the Nkx2.1+ progenitors toward dorsal MGE-like fates. As evidence suggests that the dorsal MGE domain is generated and maintained by high levels of Shh signaling compared with more ventral MGE regions (Xu et al., "Sonic Hedgehog Maintains the Identity of Cortical Interneuron Progenitors in the Ventral Telencephalon," *Development* 132:4987-4998 (2005); Wonders et al., "A Spatial Bias for the Origins of Interneuron Subgroups Within the Medial Ganglionic Eminence," *Dev. Biol.* 314 (1):127 (2008), which are hereby incorporated by reference in their entirety), and this higher level of Shh signaling contributes to the specification of Sst over PV interneuron subgroup fate (Xu et al., "Sonic Hedgehog Signaling Confers Ventral Telencephalic Progenitors with Distinct Cortical Interneuron Fates," *Neuron.* 65(3):328-40 (2010), which is hereby incorporated by reference in its entirety), future experiments will examine whether alterations in timing or concentration of Shh results in Lhx6::GFP+ cells characteristic of ventral MGE-derived interneuron types.

In sum, the Examples 1-5 are the first demonstration of the use of reporter-modified ESCs for the prospective isolation of cells with potential for developing into ventral telencephalic subpopulations following transplantation and long-term survival in vivo. An important feature of Lhx6+ cells is their ability to retain migratory capacity and neuronal commitment after transplantation into the postnatal brain without forming tumors. These studies will enable the routine use of these cells for gene discovery and studies on interneuron development and function. Access to unlimited numbers of cells exhibiting these unique properties will be useful in the development of cell-based therapies in focal epilepsy and other forebrain disorders. In addition, the prospective isolation of ESC-derived neuron types at early stages of fate commitment represents a powerful paradigm that should be applicable for generating other types of forebrain neurons.

Materials and Methods for Examples 6-10

Generation of the hES-Lhx6::GFP Line.

The previously generated Lhx6::GFP bacterial artificial chromosome (BAC) from GENSAT (Gong et al., "A Gene Expression Atlas of the Central Nervous System Based on Bacterial Artificial Chromosomes," *Nature* 425:917-925 (2003), which is hereby incorporated by reference in its entirety) was modified for G418 selection as described by Tomishima et al., "Production of Green Fluorescent Protein Transgenic Embryonic Stem Cells using the GENSAT Bacterial Artificial Chromosome Library," *Stem Cells* 25:39-45 (2007), which is hereby incorporated by reference in its entirety. This BAC, that does not express Lhx6, was electroporated into a human ESC line (WA-09 or I6, WiCell) to generate the Lhx6::GFP transgenic human ESC lines. Karyotype and FISH analysis of both human ESC lines revealed a normal chromosomal arrangement and a single BAC integration site on chromosome 14q11 (WA-09) and 17q25 (I6).

Human Cell Culture Conditions (Maintenance of Pluripotency).

Human embryonic stem cell (hESC) (WA-09 and I6; passages 42-60) and induced pluripotent stem cells (IPSC) lines (IPSC-14; passages 4-10) were cultured on mouse embryonic fibroblasts plated at 12-15,000 cells/cm2 (MEFs, Globalstem). A medium of DMEM/F12, 20% knockout serum replacement (Gibco), 0.1 mM β-mercaptoethanol, 6 ng/ml FGF-2 was changed daily. Cells were passaged using 6 U/ml of dispase in hES-cell media, washed and replated at a dilution of 1:5 to 1:10.

Neural Induction Through Dual SMAD Inhibition.

hESC and IPSC cultures were disaggregated using accutase for 30 min, washed using hES-cell media and pre-plated on gelatin for 1 h at 37° C. in the presence of ROCK inhibitor (Y27632, Tocris) to remove MEFs. The non-adherent hESCs were washed and plated on Matrigel at a density of 10,000-25,000 cells/cm2 on Matrigel (BD)-coated dishes in MEF conditioned hES-cell medium spiked with 10 ng/ml of FGF-2 and ROCK-inhibitor. Ideal cell density was found to be 20,000 cells/cm2. The ROCK inhibitor was withdrawn, and hESCs were allowed to expand in cell medium for three days or until they were nearly confluent. The initial differentiation media conditions included knockout serum replacement media with 10 nM TGF-β inhibitor (SB431542, Tocris) and 250 ng/ml of Noggin (R&D Systems). Upon day 5 of differentiation, the TGF-β inhibitor was withdrawn and increasing amounts of N2 media (25%, 50%, 75%) was added to the knockout serum replacement medium media every 2 days while maintaining 250 ng/ml of Noggin. On day 5 of differentiation, 50 ng/mL of sonic hedgehog (C25II, R&D Systems) was added to the media through day 11. After day 11, B27 (Gibco) was added to the N2 media throughout the rest of the differentiation until analysis or FACS sorting.

Immunofluorescence Analysis.

Tissue cultures were fixed using 4% paraformaldehyde for 20 min, washed with PBS, permeabilized using 0.3% triton-X in PBS, and blocked using 5% heat inactivated goat serum (HINGS) or donkey serum (HINDS) in PBS. Primary antibodies used for microscopy included rabbit anti-PAX6 (Covance), BF1 (FOXG1, gift Eseng Lai), Nkx2.1 (AB-Cam), Lhx6 (ABCam), Neuropeptide Y (Immunostar), Olig2 (gift Charles Stiles), GFP (Molecular Probes), Calretinin (Chemicon), GAD65/67 (Chemicon), Lucifer yellow (Invitrogen), and GABA (Sigma); mouse anti-human NCAM (Eric-1, ABCam), TUJ1 (Covance), Pax6 (Developmental Studies Hybridoma Bank (DSHB)), ASCL1 (BD Pharmingen), Nkx2.1 (Labvision), and Is11 (DSHB); goat anti-Nkx2.1 (C20, Santa Cruz); chick anti-GFP (ABCam); rat anti-somatostatin (Chemicon), and GFAP (Zymed). Secondary antibodies used for microscopy included Alexa fluorophores 488 and 568; Jackson Immunoresearch Cy5; and DAPI.

Preparation of primary cortical feeder cultures. Primary cortical cultures were prepared as described previously (Anderson et al., "Mutations of the Homeobox Genes Dlx-1 and Dlx-2 Disrupt the Striatal Subventricular Zone and Differentiation of Late Born Striatal Neurons," *Neuron* 19:27-37 (1997a); Xu et al., "Origins of Cortical Interneuron Subtypes," *J. Neurosci.* 24:2612-2622 (2004), which are hereby incorporated by reference in their entirety). Briefly, E13.5 embryos were harvested from killed CD1 dams and placed into ice-cold HBSS. Brains were embedded in 4% low-melt agarose (EM Science) in HBSS at 42° C. and sectioned into 300 um slices in the coronal plane using a Vibratome (Leica VT1000S). Sections were placed into Neurobasal/B27, and the periventricular proliferative zones of the cortex were dissected free. Tissues were then macerated with fine forceps, gently triturated, and then resuspended in Nb/B27 with 2% heat inactivated horse serum (HINHS, Invitrogen) medium. $1 \times 10^4$ cells in 150 ul were added to each well of 16-well chamber slides (36 mm2; Lab-Tek) or $5 \times 10^4$ cells in 500 ul were added to coverslips for electrophysiological recordings, which were both previously coated with poly-lysine (10 ug/ml) and then laminin (5 ug/ml). Cultures were maintained at 37° C. in 5% $CO_2$ and ambient oxygen. After two days in Nb/B27, the media was supplemented with 10 ng/ml of basic FGF (Promega). Media was changed every two days. After five days, 10 µM of fluorodeoxyuridine (FuDR, Sigma) was added to the media for 2 days to prevent glial over-proliferation. 500 or 2500 sorted human ESC-derived, Lhx6::GFP+ cells per well onto 16-well chamber slides or coverslips, respectively, were added to cortical feeder cultures prepared 7 days previously in Nb/B27 with 10 ng/ml of bFGF and 2% HINHS.

Electrophysiological Recordings of Human Cells In Vitro.

Whole-cell recordings were made from Lhx6-GFP+ WA-09 human ESC-derived neurons. Lhx6::GFP+ interneuron precursor cells were sorted and plated on a mouse cortical feeder previously grown for seven days and treated with FUDR (5-fluoro-2-deoxyuridine, Sigma) to prevent glial overgrowth. Nearly all GFP+ cells recorded were capable of firing action potentials between 11 DAP (days after plating) and 21 DAP. Patch electrodes were made from borosilicate glass (Sutter Instrument Co., Novato, Calif.) and had a resistance of 5-8 MΩ when filled with intracellular solution. The intracellular solution contained (in mM) 130 K-gluconate, 4 NaCl, 0.3 GTP, 0.5 GTA, 5 ATP, and 10 HEPES, pH 7.25. For postrecording immunohistochemistry, 0.2% Lucifer yellow was also included in the intracellular solution. The standard extracellular solution contained (in mM) 145 NaCl, 10 HEPES, 6 D-glucose, 3 KCl, 1 MgCl2, and 1.5 CaCl2, pH 7.5. The osmolarity of the intra- and extracellular solutions were, 280 and 300 mOsm, respectively. Human cells had a larger diameter than the mouse feeder cells and were more neuron-like in morphology. Cells were recorded in current-clamp mode at room temperature (21±1° C.) using Axopatch 200A amplifier (Molecular Devices, Sunnyvale, Calif.). All recordings were performed in current-clamp mode and analyzed off-line with Clampfit version 10.1 (Molecular Devices). The membrane potential was manually adjusted to −60 mV. Standard current-step protocols were used to elicit action potentials. Passive membrane properties, such as membrane potential and input resistance, were ascertained shortly after rupturing the patch and periodically during the course of the experiments to ensure that there was no significant deterioration in the recording conditions of the cell. After recordings were completed, the electrode was carefully withdrawn from the cell. Fluorescence microscopy was then used to ensure thorough filling with dye, and a detailed description of the cell's morphological and position on the coverslip was made to identify each cell with its corresponding recorded action potentials. A maximum of three neurons were recorded from each coverslip. Cells were fixed for twenty minutes at room temperature with 4% paraformaldahyde/PBS solution and stored at −4° C. until immunofluorescent analysis for neurochemical markers of interneurons.

Example 6

Rapid Differentiate of hESCs into Telencephalic Progenitor Cells Characteristic of Mouse-Derived Interneuron Precursors While several protocols have been described to enrich for telencephalic cell types from human ESCs (Watanabe et al., "A ROCK Inhibitor Permits Survival of Dissociated Human Embryonic Stem Cells," *Nat Biotechnol* 25(6):681 (2007) and Li et al., 2009, which are hereby incorporated by reference in their entirety), these protocols often take more than 4 to 8 weeks. A recent study described a more rapid and defined neural induction paradigm based on the dual inhibition of SMAD signaling through exposure to Noggin and SB431542 (NSB protocol) (Chambers et al., "Highly Efficient Neural Conversion of Human ES and iPS cells by Dual Inhibition of SMAD Signaling," *Nat. Biotechnol.* 27:275-280 (2009), which is hereby incorporated by reference in its entirety). Here, the NSB protocol was modified by treating with the morphogen Sonic Hedgehog (SHH) at differentiation day (dd) 5 through dd11 (FIG. 10A) and assaying for NKX2.1 expression at dd11 (FIGS. 10B and 10C) and dd18 (FIGS. 10D-10G). In mouse, SHH is required upstream of NKX2.1 for the initial patterning of the NKX2.1 domain in the MGE (Fuccillo et al., "Temporal Requirement for Hedgehog Signaling in Ventral Telencephalic Patterning," *Development* 131:5031-5040 (2004), which is hereby incorporated by reference in its entirety), and to maintain NKX2.1 expression in progenitors during neuronogenesis (Xu et al., "Sonic Hedgehog Maintains the Identity of Cortical Interneuron Progenitors in the Ventral Telencephalon," *Development* 132(22):4987 (2005), which is hereby incorporated by reference in its entirety). Although the NSB protocol highly enriched for BF1/FOXG1-expressing, PAX6-expressing human neural cells (FIG. 10B, bottom panel), only treatment with SHH significantly increased the levels of NKX2.1 expression, which significantly overlapped with BF1/FOXG1 and PAX6 expression (FIG. 10C). It was previously reported that NKX2.1 (Rakic et al., "Emerging Complexity of Layer I in Human Cerebral Cortex," *Cereb. Cortex* 13:1072-1083 (2003a), which is hereby incorporated by reference in its entirety) and OLIG2 (Jakovcevski et al., "Olig Transcription Factors are Expressed in Oligodendrocyte and Neuronal Cells in Human Fetal CNS," *J. Neurosci.* 25:10064-10073 (2005), which is hereby incorporated by reference in its entirety) in the human embryonic brain, unlike in rodent brains, is expressed from the ganglionic eminence (GE) into the cortical VZ and the cortical plate from early developmental stages, whereas both genes are markers of the MGE-derived interneuron precursors in mouse (Miyoshi et al., "Physiologically Distinct Temporal Cohorts of Cortical Interneurons Arise from Telencephalic Olig2-Expressing Precursors," *J. Neurosci.* 27:7786-7798 (2007), which is hereby incorporated by reference in its entirety).

In order to determine if the NSB protocol is capable of eventually giving rise to telencephalic cells expressing markers of interneuronal cell fate, the duration of differentiation was extended to 18 days (dd18). To this end, the NKX2.1 expressing population of cells was characterized. Although a few of the differentiated cells in the NSB protocol expressed NKX2.1 and OLIG2, nearly all of the cells treated with SHH expressed NKX2.1 and OLIG2 (FIG. 10D). Further characterization of these NKX2.1+ cells in the SHH treated condition at dd18 revealed that many continued to co-express BF1/FOXG1 as well as ISL1 (FIG. 10E). The three markers combined can be considered reflective of a ventral telencephalic progenitor that could potentially give rise to cholinergic cell populations (Fragkouli et al., "LIM Homeodomain Transcription Factor-Dependent Specification of Bipotential MGE Progenitors into Cholinergic and GABAergic Striatal Interneurons," *Development* 136:3841-3851 (2009), which is hereby incorporated by reference in its entirety). Most of the cells transition from neuroepithelial ridges at dd11 to neural tube-like progenitors by dd18. Unlike the significant overlap between NKX2.1 and PAX6 at dd11 (FIG. 10C, bottom panel), the NKX2.1-expressing cells appeared adjacent to the PAX6-expressing cells at dd18, suggesting that the telencephalic progenitors may segregate into pallial and subpallial domains (FIG. 10F). Many of these NKX2.1-expressing cells co-label with ASCL1, a marker expressed by human (Letinic et al., "Origin of GABAergic Neurons in the Human Neocortex," *Nature* 417:645-649 (2002), which is hereby incorporated by reference in its entirety) and primate (Petanjek et al., "Origins of Cortical GABAergic Neurons in the Cynomolgus Monkey," *Cereb. Cortex* 19:249-262 (2009), which is hereby incorporated by reference in its entirety) dorsally-derived interneuronal precursors (FIG. 10G). These transcription factor combinations aid in the definition of human telencephalic regions that either diverge from or are conserved with rodents and primates.

Example 7

Generation and Characterization of the Lhx6::GFP hESC Lines

LHX6 is highly enriched in the fetal human forebrain, and continues to be expressed in adult human cortex Su et al., "A Gene Atlas of the Mouse and Human Protein-Encoding Transcriptomes," *Proc. Natl. Acad. Sci. USA* 101:6062-6067 (2004), which is hereby incorporated by reference in its entirety. Since Lhx6 expression is initially activated by NKX2.1 in the MGE of mice, and the binding domain for NKX2.1 on the LHX6 promoter is 100% conserved between mice and humans (Du et al., "NKX2.1 Specifies Cortical Interneuron Fate by Activating Lhx6," *Development* 135:1559-1567 (2008), which is hereby incorporated by reference in its entirety), transgenic, human embryonic stem cell (hESC) lines harboring the mouse Lhx6-GFP BAC construct were created using a protocol for stable integration of BACs (Placantonakis et al., "Bac Transgenesis in Human Es Cells as a Novel Tool to Define the Human Neural Lineage," *Stem Cells* 27:521-532 (2009), which is hereby incorporated by reference in its entirety) into both the WA-09 (XX) and the I-06 (XY) hESC lines. Both the WA-09 (C8) and I-06 (124) Lhx6::GFP hESC lines did not exhibit any karyotypic abnormalities and each line revealed a single BAC integration site at 14q11 and 17q25, respectively (red dots, FIG. 11A). Using the SHH protocol (FIG. 10A), the 12.4 Lhx6::GFP line was analyzed at dd25, because GFP was not detectable at dd11 or dd18. FACS analysis at dd25 shows a GFP+ population clearly segregating from the autofluorescent band, with a yield of approximately 0.5-1% of the living cells (FIG. 11B). Enrichment of the LHX6 transcript was found in the sorted GFP+ cells over the GFP− cells by qRT-PCR analysis (FIG. 11C). Analogous to its expression in mice where LHX6 expression turns on in the last cell division in the MGE (Du et al., "NKX2.1 Specifies Cortical Interneuron Fate by Activating Lhx6," *Development* 135:1559-1567 (2008), which is hereby incorporated by reference in its entirety), the GFP+ cells appear on the periphery of several rosette-like clusters, suggesting that they are also in their last cell division Elkabetz et al., "Human ES Cell-Derived Neural Rosettes Reveal a Functionally Distinct Early Neural Stem Cell Stage," *Genes Dev.* 22:152-165 (2008), which is hereby incorporated by reference in its entirety) and have neuronal morphologies with a prominent leading process similar to that of migrating interneurons (FIG. 11D). Using immuno-fluorescent characterization of the Lhx6::GFP line at dd25, before FACS analysis, many GFP+ cells were observed in streams along BF1+/FOXG1+ domains and appeared to emanate from NKX2.1-expressing cells that often co-expressed BF1/FOXG1 (FIGS. 11E-11E4). These GFP-expressing, NKX2.1-expressing cells were also labeled by OLIG2 (FIGS. 11F-11F4), and ASCL1 (FIGS. 11G-11G4) suggesting that pallial and subpallial progenitors of the forebrain are being generated.

Example 8

Maturation of hESC-Derived Lhx6::GFP+ Progenitors into Distinct Groups of Interneuron-Like Cells Unlike mouse ESC-derived Lhx6::GFP cells, most of the hESC-derived Lhx6::GFP+ progenitors did not clearly co-label with GABA, which can be explained through several scenarios. First, detection of GABA by immunostaining can be inconsistent due to the lack of glutaraldehyde in the fixative, which when added, significantly decreased the detectability of GFP. Second, the human interneuronal precursors of the LHX6 lineage may not express detectable levels of GABA as soon as mouse cells do. Third, in humans there may be a substantial population of LHX6-expressing cells that are not GABA-expressing interneurons. Fourth, the in vitro environment created by differentiating human ESCs may not be sufficient for GABA specification in the timeframe of analysis. In order to test whether the cortical environment could affect the maturation process of human Lhx6::GFP+ cells into GABAergic interneurons, a cortical feeder environment was created using embryonic day (E13.5) mice cortical cells. This approach provided a feeder environment containing an even ratio of neurons to glia without a large portion of interneurons, since many have not completed their migration into the cortex at that age. Because the E13.5 cortex was highly proliferative, the cortical feeder cultures were treated with fluoro-deoxyuridine (FuDR) 5 days after plating (DAP) in order to reduce mitotic events.

To determine whether Lhx6::GFP+ cells could give rise to cortical GABAergic interneurons in vitro, hESCs were differentiated for 32 days, FACS sorted for GFP-expression, then plated onto neocortical feeder layers generated 7 days prior (FIG. 12A). After 1 day, the GFP+ cells consistently co-labeled with human neural cell adhesion molecule (hN-CAM) (96.9+/−1.9%, n=2) (FIGS. 12B and 12D, expressed the neuronal marker TuJ1 (93.4+/−3.9%, n=2) (FIGS. 12C-12D), and exhibited a migratory neuronal morphology with a leading process. The GFP+ cells did not co-label with GFAP or nestin. After 10 days, many of the GFP+ cells expressed the neurotransmitter GABA together with TuJ1 (FIG. 12E).

After 17 days, GFP expression was weakly detectable even with three different primary antibodies (FIGS. 12F, and 13D1). Because hNCAM only stained the human-derived cells in the xenograft cultures and clearly labeled the morphology of the Lhx6::GFP+ neurons (FIG. 12D), it was used to label the human-derived progenitors with neurochemical markers of interneurons (FIG. 12F1). Consistent with the GABA staining seen at 10 DAP, many of the hNCAM+ neurons expressed the enzymes GAD65 and GAD67 (FIG. 12G, green signal pseudocolored from Cy5 channel), suggesting that the human cells are inhibitory neurons capable of synthesizing GABA. Some of these hNCAM+ cells (red) also expressed either neuropeptide Y (NPY; FIG. 12H) or calretinin (CR; FIG. 12I, green signal pseudocolored from Cy5 channel), both being neurochemical markers expressed by cortical interneurons. This data suggests that after 17 days in culture on a mouse-derived cortical environment, Lhx6::GFP+ cells are capable of becoming distinct subgroups of cortical inhibitory interneurons.

Example 9 hESC-Derived, Lhx6::GFP+ Cells Exhibit Physiological and Neurochemical Characteristics of Cortical Interneurons Since the Lhx6::GFP+ cells were capable of expressing the neurochemical markers of interneuron subgroups, whether these cells also exhibited the same electrophysiological properties as mouse interneurons was determined. Very few studies have characterized the firing properties of human interneurons together with neurochemical markers (Olah et al., "Output of Neurogliaform Cells to Various Neuron Types in the Human and Rat Cerebral Cortex," *Front Neural Circuits* 1:4 (2007) and Molnar et al., "Complex Events Initiated by Individual Spikes in the Human Cerebral Cortex," *PLoS. Biol.* 6:e222 (2008), which are hereby incorporated by reference in their entirety). Using the cortical feeder system (FIG. 12A), whole-cell patch clamp recordings were performed on sorted GFP+ cells plated on glass coverslips. Using size exclusion to identify the human cells, a total of 16 cells between 11-21 DAP were recorded having an average resting membrane potential of −42.18+/−7.4 mV. After recording, each cell was filled with lucifer yellow (LucY) for neurochemical analysis. After 11 days, although the GFP+ cells immunolabeled for LucY, they failed to express SST (n=3; FIG. 13A). These cells elicited discharges at 1× threshold (FIG. 13B), but failed to maintain consistent firing patterns at 2× threshold (FIG. 13C), suggesting that these cells were immature neurons at this age.

After 18 days, one cell exhibited a neuronal morphology (FIG. 13D), co-expressed GFP (FIG. 13D1), and expressed the interneuron subgroup marker somatostatin (SST; blue signal pseudocolored from Cy5, FIG. 13D2). When subjected to current injections, this cell exhibited a regular spiking, non-accommodating firing response to depolarization at ~3× threshold, a firing pattern sometimes seen in mouse-derived SST+ interneurons (FIG. 13F).

When this same cell was voltage-clamped at 0 mV, spontaneous burst spiking activity was observed (FIG. 13G). Taken together, this data indicates that the human ESC-derived Lhx6::GFP+ cells are capable of exhibiting interneuron-like firing properties after 18 days in the mouse cortical feeder environment.

Example 10

Induced Pluripotent Stem Cells (IPSCs) Differentiate into Lhx6::GFP-Expressing, GABAergic Neuronal Progenitor Cells Recent publications have reported the derivation of IPSCs from adult somatic cells Takahashi et al., "Induction of Pluripotent Stem Cells from Adult Human Fibroblasts by Defined Factors," *Cell* 131:861-872 (2007); Park et al., "Reprogramming of Human Somatic Cells to Pluripotency with Defined Factors," *Nature* 451:141-146 (2008); Kaji et al., "Virus-Free Induction of Pluripotency and Subsequent Excision of Reprogramming Factors," *Nature* 458:771-775 (2009); and Papapetrou et al., "Stoichiometric and Temporal Requirements of Oct4, Sox2, Klf4, and c-Myc Expression for Efficient Human iPSC Induction and Differentiation," *Proc. Natl. Acad. Sci. USA* 106:12759-12764 (2009), which are hereby incorporated by reference in their entirety). Whether the SHH protocol was capable of driving IPSCs to rapidly produce cortical interneuronal progenitors that express Lhx6::GFP was investigated. In order to expedite the process of generating interneuronal precursors without the need to create stably expressing Lhx6::GFP BAC lines, a 2 kilobases (KB) fragment of the mouse Lhx6 gene, which contains both a 0.8 KB 5' region and the first intron of the Lhx6 gene was used to express GFP as a means to report on Lhx6 expression in human cells. This construct contains the Nkx2.1 binding domain in the Lhx6 promoter that is 100% conserved between mouse and human (i.e., SEQ ID NO:3) and is 87% conserved overall with the human sequence by BLAST analysis (Du et al., "NKX2.1 Specifies Cortical Interneuron Fate by Activating Lhx6," *Development* 135(8): 1559 (2008), which is hereby incorporated by reference in its entirety). This 2 KB Lhx6::GFP construct was validated in embryonic brain slice electroporations and its expression was maintained in Lhx6-derived interneurons several weeks after transfection (Du et al., "NKX2.1 Specifies Cortical Interneuron Fate by Activating Lhx6," *Development* 135: 1559-1567 (2008), which is hereby incorporated by reference in its entirety).

After differentiating the IPSCs to dd25 using the SHH protocol (FIG. 10A), when most of the cells are expressing BF1/FOXG1, Nkx2.1, ASCL1, Olig2, and Pax6, the 2 KB Lhx6::GFP construct was nucleofected into the dissociated cells and the cultures were grown for an additional 7-17 days (dd32-dd42). Seven days after nucleofection (dd32), many of the cells expressed GFP (1-2%) and all appeared to have neuronal morphologies with growth cone processes (FIG. 14C). After FACS sorting (FIG. 14A), the GFP+ cells were enriched for Lhx6 transcript (144+/−3 fold) over the GFP− cells (FIG. 14B) as shown by qRT-PCR analysis. This result indicates that the 2 KB Lhx6::GFP construct provides a means to enrich for cells that express for LHX6.

In order to determine if the IPSC-derived cells were capable of generating the same interneuronal progenitors as the BAC transgenic hESC-derived, GFP+ cells, immunolabeling for ventral telencephalic markers was performed. This analysis revealed that the IPSC-derived GFP+ cells reliably expressed the NKX2.1, OLIG2, and ASCL1 (FIGS. 14D-14E3). Similar to the observations in hESC-derived cultures at dd25, the IPSC-derived GFP+ progenitors co-labeled with Nkx2.1 as well as Pax6, suggesting that a pallial domain for interneuron genesis may exist in humans (FIGS. 14F-14F3). After 17 days post nucleofection (dd42), a few of the GFP+ cells differentiated into GABA-expressing, TuJ1+ neurons (FIGS. 14G-14G3). Taken together with the results using the Lhx6::GFP BAC, these results indicate that the SHH protocol offers a robust method to derive cortical interneuron progenitors that can be isolated from human pluripotent stem cells using multiple constructs of the LHX6 promoter.

Discussion of Example 6-10

Development of the human forebrain depends on multiple progenitor domains to generate diverse cell types. Human ESC and iPSC technology presented in these Examples make it possible to observe the complex transcriptional cascades that specify distinct neuronal progenitor cell types in human cortical development without the use of aborted fetuses. In many directed differentiation paradigms for human pluripotent stem cells, the telencephalon is considered to be the default region of neural induction, with most cells forming patternable neural rosettes in culture after 30 days (Elkabetz et al., "Human ES Cell-Derived Neural Rosettes Reveal a Functionally Distinct Early Neural Stem Cell Stage," *Genes Dev.* 22:152-165 (2008); Li et al., "Coordination of Sonic Hedgehog and Wnt Signaling Determines Ventral and Dorsal Telencephalic Neuron Types from Human Embryonic Stem Cells," *Development* 136:4055-4063 (2009); Wantanabe et al., "A ROCK Inhibitor Permits Survival of Dissociated Human Embryonic Stem Cells," *Nat. Biotechnol.* 25:681-686 (2007); Eiraku et al., "Self-Organized Formation of Polarized Cortical Tissues from ESCs and its Active Manipulation by Extrinsic Signals," *Cell Stem Cell* 3:519-532 (2008); and Chambers et al., "Highly Efficient Neural Conversion of Human ES and iPS cells by Dual Inhibition of SMAD Signaling," *Nat. Biotechnol.* 27:275-280 (2009), which is hereby incorporated by reference in its entirety). Using the protocol described herein, cells with dorsal and ventral telencephalic fate were generated within 11 days (FIG. 10). This protocol was reliably used to differentiate hESCs and IPSCs into LHX6-GFP+ interneuronal precursors that also express NKX2.1, OLIG2, ASCL1, PAX6, ISL1, and BF1/FOXG1. While most of the cells are NKX2.1+ after 18 days, the percentage of GFP-expressing cells by FACS (0.5-2%) is rather low. In the human forebrain, NKX2.1 expression is only in the GE and preoptic area (POA) at gestational week (gw) 5 (35 days) and arises in the cortical VZ/SVZ from 8-15 gw (Rakic et al., "Emerging Complexity of Layer I in Human Cerebral Cortex," *Cereb. Cortex* 13:1072-1083 (2003), which is hereby incorporated by reference in its entirety).

In this study, many of the NKX2.1+ cells co-labeled with ISL1 (FIG. 10E), a marker of POA cells that mainly give rise to cholingeric projection neurons of the septum (Fragkouli et al., "Loss of Forebrain Cholinergic Neurons and Impairment in Spatial Learning and Memory in LHX7-Deficient Mice," *Eur. J. Neurosci.* 21:2923-2938 (2005) and Fragkouli et al., "LIM Homeodomain Transcription Factor-Dependent Specification of Bipotential MGE Progenitors into Cholinergic and GABAergic Striatal Interneurons," *Development* 136:3841-3851 (2009), which are hereby incorporated by reference in their entirety). In the human system, NKX2.1+ cells may need to undergo several rounds of cell division before becoming post-mitotic interneuron precursors that express LHX6. There may also be subtle yet significant differences between the mouse and human LHX6 promoter that can cause a decrease in GFP signal intensity detected by FACS.

In mice, Lhx6 is expressed in most or all medial ganglionic eminence-derived interneurons from around the time of cell cycle exit through post-natal development. Details of LHX6 expression in human are not known, but it appears to be enriched in the embryonic telencephalon (Su et al., "A Gene Atlas of the Mouse and Human Protein-Encoding Transcriptomes," *Proc. Natl. Acad. Sci. USA* 101:6062-6067 (2004), which is hereby incorporated by reference in its entirety). Examples 6-10 provide evidence connecting the expression of Lhx6 with several genes known to be involved in the development of interneurons, including ASCL1, OLIG2, and NKX2.1. The NKX2.1 binding site and much of the putative promoter region of Lhx6 is conserved between mouse and humans (Du et al., "NKX2.1 Specifies Cortical Interneuron Fate by Activating Lhx6," *Development* 135:1559-1567 (2008), which is hereby incorporated by reference in its entirety), suggesting that the mouse Lhx6-GFP BAC and the 2KB Lhx6-GFP constructs function to express GFP in LHX6-expressing human cells. This was successfully demonstrated through the transient transfection of differentiated IPSCs, which is a highly useful method to isolate interneuronal precursors from patternable stem cells. Although most Lhx6::GFP+ cells are considered to be ventrally-derived interneuronal precursors of the forebrain, the data presented herein indicates that they may also be expressing the dorsal gene, PAX6 (FIGS. 14F-14F3). Experiments inhibiting or enhancing expression of Pax6 or Nkx2.1 in the differentiation paradigm would allow their effects on the development of LHX6+ cortical interneurons to be tested and to draw conclusions on their involvement in increasing evolutionary complexity of the human forebrain.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. An isolated or a purified preparation of human cortical immature interneuron precursor cells, wherein the human cortical immature interneuron precursor cells of the preparation comprise an exogenous recombinant nucleic acid molecule encoding a marker protein or a therapeutic agent, said recombinant nucleic acid molecule operably linked to at least one of a Lhx6 promoter region and a Lhx6 enhancer region.

2. The isolated or the purified preparation of claim 1, wherein the human cortical immature interneuron precursor cells of the preparation comprise a genomic ally integrated bacterial artificial chromosome.

3. The isolated or the purified preparation of claim 1, wherein the therapeutic agent is selected from the group consisting of neuropeptide Y, galanin, adenosine, and GABA.

4. The isolated or the purified preparation of claim 1, wherein said recombinant nucleic acid molecule is genomically integrated into the cells.

* * * * *

UNITED STATES PATENT AND TRADEMARK OFFICE
CERTIFICATE OF CORRECTION

PATENT NO.        : 9,487,751 B2
APPLICATION NO.   : 13/376039
DATED             : November 8, 2016
INVENTOR(S)       : Anderson et al.

It is certified that error appears in the above-identified patent and that said Letters Patent is hereby corrected as shown below:

In the Specification

Column 1 at Lines 11-15, delete "This invention was made with government support under grant number IF 31 MHO 79664-01A1 awarded by the National Institute of Mental Health and grant number 5R01MH066912 awarded by the National Institutes of Health. The government has certain rights in this invention." and insert --This invention was made with government support under grant numbers MH066912 and MH079664 awarded by the National Institutes of Health. The government has certain rights in the invention.--

Signed and Sealed this
Eighth Day of May, 2018

Andrei Iancu
*Director of the United States Patent and Trademark Office*

SEQUENCE LISTING

<160> NUMBER OF SEQ ID NOS: 3

<210> SEQ ID NO 1
<211> LENGTH: 2081
<212> TYPE: DNA
<213> ORGANISM: Mus musculus

<400> SEQUENCE: 1

```
cagcctttag aagctggtgc aagctccggt tgtcatgaag cagggatatt tttgcaggag        60
tttgaggggt gtgtcgaagt ctaggacctg aaggattggt gtgagcaggt gaccatttgc       120
gacacaaata taccaggctc agcactacat caacagaacg tggcttcatg tggaatccag       180
ccttgtagat gggctgacca cggattcctc tcgcacctat taacgttgtg tgagggcggc       240
agtgggtgcc cttgagggag gggcggcaga aggagctgtg aggatatgtg ccccgccagt       300
gtctttgtat gttagcatgt tccaagagtc tccctgtagc gcctagtttc agtgtgtctc       360
```

```
tctgtgtgtg tatgtctctg agtctctgcc tcctttggag tgtctcgctc ttcttagcgg    420
ggaggggatt ggtcacgcat gactcatctt gaacggagcg gggctccagc ggcagggcgg    480
tcgtcgccgc agctggaagg ggaggaggac aacgaggagg agaacagga ggaggaagag     540
gaggaggagg aagaggagga ggaggcggca gccgcagaag cagctgcagg gacctctcca    600
agtttgtcgg gaccttcttc agaggcagtg gtgctggcag ccagggaggc caggactgcg    660
ctcaggccgg gggcggggag ctggggctgg gccggggcg gcggggccgg agcctcggtt     720
ctccagctct cccagcagcc tctgccccca ggacgcccga ggccccactc tgcgcctctc    780
ttcgcactgc gcgcccaccg agccctcccg ctcccgggcc catgtactgg aagcatgaga    840
gcgccgcccc ggcgctgccc gagggctgcc ggttgccggc ggagggcggc cccaccaccg    900
accaggtgag caagcaggcg agtgggtgag cgtcggggat cctggggcca gcggagccg     960
ggattcaacc gggccgggtc gggtggcggg cggcagcagg aaggaggggt gctgagtgag   1020
cccgggagag tgtgtctgca agtgtgtgag cgtgcgagcg ggcaggcggg ggtgggggt    1080
cgcggaaagc gggaacacat tatgcaaatg ttggaggaat ttctcaaaaa gcgatttagc   1140
aaagacatag gcgaatcaag aggaggcgag gccagtattg ccgtctgaa tagacgctga    1200
tagcgccgat gcgccagagg ttgtgccggc gcaacgctga ggatctcgat gaggggccgg   1260
tcccgggagc tccaagagtc tggagggttc tctttcctcc tccaagaggc ctctcttttc   1320
tcttttggc ctcatttcac tcgccgatct cgccctcttt ggcttgggc ttcccttgaa     1380
ctggccctcc aaaggcgttt gaatcggtgt caatatcccc gcttcaattt cccggcgcgc   1440
gtcgagcggc cggatgctcc tagcgctctg ggttttattt tctcaaccac caccaccact   1500
accaccacca ccaccccat ctccttttta ttttcttct ttctctcttt tctccttttt     1560
gcattttgta ccgagagtag gagaaggag ggggcggagg gagaaaaaaa ttcgattttt    1620
aattactacc attaaaaaat caaatttgca attctttggg cggcctgatg gatctcactg   1680
attgacagtt ggaattgaca ctctggctac ctcttatctt gggcattcac gacaatttct   1740
aattgcaggt agtttgtgtg tgtgcgcgtg tttttttttcc ccctcagagg cttggattgc   1800
aaaggaacta agcgattact tcaagagcca cgggttaagt gcaggagag ggggagagag    1860
agggaaaaaa acccaatcca aattcaaatt gcttcattag agagacaccg cttttgtggg   1920
gaagggcttt aaatgcccac tacaaagtta ggactcattg ttcagcgccg gtttatataa   1980
caggcgaggg gaggcgctgg gctctgacag ctccgagcca gttcagcagc cgccgtcgcc   2040
tgcattccct cccctcccc caggtgatgg cccagccagg g                       2081
```

<210> SEQ ID NO 2
<211> LENGTH: 2398
<212> TYPE: DNA
<213> ORGANISM: Homo sapiens

<400> SEQUENCE: 2

```
gaaggggggct gagactctaa gtgtccactt gtgtatgctg cagggcgtta gtgtgtgtaa    60
ggctccatct ttgggtttga aggttctgtg tctgtgtgtc tgggggcagt gtcttctgtc   120
taaatgcctg ggccttcctg ccttccctac cattctcatt gtcagtagaa ccctagagaa   180
gaagggatgg gcattggact gtgtggttaa gcaaatcctg aagggaaggg gaatgtgcca   240
agcaatccct tccaagagaa ttcagggaaa ctaccctccc gtttcacctc agtccctggg   300
agctggtgca ctgtctggtt cttatagagc agaggtatct gtgcaggtgt gtgagagtaa   360
gtgtggtgcc tcgtgcccgt gtaaatgatg tgaacaggta atcacttaca ttagtgtgta   420
```

| | |
|---|---|
| cacaaatgta ccaggcatgg gattgcatca acacagtgta ataacgtgtg acctcctacg | 480 |
| gaatctatct ccgcagatgg tatggccatg ggtccctcct gtacctgtga gtggggcagt | 540 |
| gtctgaggaa gatgggtgcc ccttgaggga ggagcggtag tgagagctgg gtggatgtgt | 600 |
| gcccgccggt gcctttgtgt actgcgtgt ctccgagtct ctctgtcggc agctctgagt | 660 |
| ttctgtgtgt ctctgtgtct gtgtgtgtgt ctctctctct gggtctctgc ctcgtcgtgt | 720 |
| gtgtcttgct ctcccttggc ggggagggga ttggtcacgc atgactcatc ttgaaccgag | 780 |
| cggggctcca gcggcagggc ggccgccgtt gcagctggag ggggaggagg acaaggagga | 840 |
| gggagaggag gaggaggact accaagaggg ggaggaggag aagaaggagg gggcgggggc | 900 |
| ctctccaagt ttgtcgggac cttcttccga ggcagcggcg gcagcagcca gggaggccgg | 960 |
| ggctgcgcgc gggccggggg cggggctga ggccgggccc ggggcggcgg ggccggcgcc | 1020 |
| tcggctctcc tcctgctcct gcagcagcct ctgctcccac tgcggctgtg gtcccctcg | 1080 |
| gcgcagctct ccgcgctgcg cgcccgctga gcccgaggtt ccccggccca tgtactggaa | 1140 |
| gcatgagaac gccgccccgg cgttgcccga gggctgccgg ctgccggccg agggcggccc | 1200 |
| cgccaccgac caggtgagcc ggcgaacgac tgggtgagcg gcccgggccg gggtcgggca | 1260 |
| gggtccggga cccagccggg ccgagcaggg tggcgggcg ttgcaggaag gaggggtacg | 1320 |
| agggtgcgcc tgtgagtgtg tgcttgtgag tgtgggagcg cgcgcgcgag cggggggggg | 1380 |
| gggtcgcgga aagcgggaac acattatgca aatgttggag gaatttctca aaaagcgatt | 1440 |
| tagtaaagac acaggcgaat caagaggagg cgaggccggt attgtccgtc tgaataggcg | 1500 |
| ctgatagcgc cgatgcgccg ggggttgtgc cggcgcagcc tgagaatcc cgacgcgggg | 1560 |
| ccggtacccg gcgcgccgag gggctggagg gtgctttttc ctccccttga gcgcctctct | 1620 |
| tttctctttt tggtcccgtt tcgccccgat ctcgctctct ttttgctccg ggtttccctc | 1680 |
| cgactggccc tcgaaaggcg cctgaatccg tgtcaatata gctgcttcaa tttcgccgcg | 1740 |
| cgtgtcaggc gggcgggcgg gcgggtgctc accgcgctcg gggttttctt ttcttcaacc | 1800 |
| accctccgcc cctcacccat ctcttttta ttttctttct ttctctcttt tctcctttt | 1860 |
| gcattttgtg ccgagaggag aagggagcga ggaaggggag tggggtgggg gggcgggtgg | 1920 |
| agagagaaaa aattcgattt taattacta ccattaaaaa atcaaatttg caattctttg | 1980 |
| ggcggcctga tggatctcac tgattgacag ttggaattga cactctggct acctcttatc | 2040 |
| ttgggcattc acgacaattt ctaattgcag gtagtttgtg tgtgtgtgcg cgtgtttttc | 2100 |
| ttccccctc agaggcttgg attgcaaggg aactaagcga ttacttcaag agccacgggt | 2160 |
| taagtgcagg gagaggggga gagagaggga aaaaatccaa tccaaattca aattgcttca | 2220 |
| ttagagagac accgcttttg tggggaaggg ctttaaatgc ccactacaaa gttaggactc | 2280 |
| attgttcggc gccggtttat ataacaggcg cggggaggcg ctgggctcag gctgtgcgga | 2340 |
| gccagttcag cagccgccgc cgcctgcgtt ccctcccccc ctcccccagg tgatggcc | 2398 |

```
<210> SEQ ID NO 3
<211> LENGTH: 32
<212> TYPE: DNA
<213> ORGANISM: Artificial
<220> FEATURE:
<223> OTHER INFORMATION: Nkx2.1 binding domain

<400> SEQUENCE: 3
```

| | |
|---|---|
| cttgattcgc taatgaagtt ctcggtgccc aa | 32 |